United States Patent
Zweig

(10) Patent No.: US 7,291,698 B2
(45) Date of Patent: Nov. 6, 2007

(54) SYNTHETIC SUBSTRATE FOR HIGH SPECIFICITY ENZYMATIC ASSAYS

(76) Inventor: Stephen Eliot Zweig, 224 Vista de Sierra, Los Gatos, CA (US) 95030

( * ) Notice: Subject to any disclaimer, the term of this patent is extended or adjusted under 35 U.S.C. 154(b) by 653 days.

(21) Appl. No.: 10/233,908

(22) Filed: Sep. 3, 2002

(65) Prior Publication Data

US 2003/0113768 A1    Jun. 19, 2003

Related U.S. Application Data

(60) Provisional application No. 60/317,023, filed on Sep. 4, 2001.

(51) Int. Cl.
*C07K 2/00* (2006.01)
*G01N 33/53* (2006.01)
*C12Q 1/37* (2006.01)
*C12N 11/00* (2006.01)

(52) U.S. Cl. .................. 530/300; 435/7.72; 435/23; 435/174

(58) Field of Classification Search .................. 435/23, 435/7.72, 174, 28, 212–219; 530/300, 800, 530/324–332
See application file for complete search history.

(56) References Cited

U.S. PATENT DOCUMENTS

| | | | |
|---|---|---|---|
| 4,247,454 A | 1/1981 | af Ekenstam et al. |
| 4,557,862 A | 12/1985 | Mangel et al. |
| 4,897,444 A | 1/1990 | Brynes et al. |
| 5,413,854 A | 5/1995 | Sato |
| 5,418,143 A | 5/1995 | Zweig |
| 5,580,747 A | 12/1996 | Shultz et al. |
| 5,605,809 A | 2/1997 | Komoriya et al. |
| 5,741,659 A | 4/1998 | Ralls et al. |
| 6,037,137 A | 3/2000 | Komoriya et al. |
| 6,248,904 B1 | 6/2001 | Zhang et al. |
| 2003/0186345 A1* | 10/2003 | Hortin ........................ 435/23 |

OTHER PUBLICATIONS

Tung et al. "In vivo imaging of proteolytic enzyme activity using a novel molecular reporter," J. Cancer Res. (Sep. 2000) 60: 49534958.*
Benacerraf et al. "Artificial antigens. II. The antigenicity in guinea pigs of arsanilic acid conjugates of copolymers of D- or L-alpha-amino acids," J. Experimental Med. (1963) 118(6): 945-952.*
Hugues et al. "Conjugation of methotrexate to Poly(L-lysine) as a potential way to overcome drug resistance" Cancer (1980) 54: 1207-1211.*
Anjuere et al. "Sensitive, hydrosoluble, macromolecular fluoregenic substrates for human immunodeficiency virus 1 proteinase," Biochem. J. (1993) 291: 869-873.*
King, t. "Immunological properties of protein conjugates with non-immunogenic polymers: Studies wit ragweed pollen allergen, antigen E." Versitility Proteins, [Proc. Int. Symp. Proteins] Ed: Li, D. (Academic: New York, NY) (1978) 335-351.*
Liu et al. "New procedures for preparation and isolation of conjugates of proteins and a synthetic copolymer of D-Amino Acids and immunochemical characterization of such conjugates" Biochemistry (1979) 18(4):690-697.*
Harris et. al., Proc. Natl. Acad. Sciences (2000); 97(14), 7754-7759.
Lam and Lebl, Methods Mol. Biol. (1998); 87: 1-6.
Folkman et. al., Thromb. Haemost (2001); 86: 23-33.
Knight, Methods in Enzymology (1995); 248: 18-34.
Groutas, et. al., Bioorg Med. Chem. (2001); Jun. 9(6): 1543-1548.
Fodor et. al., Science (1991); 251: 767-773.
MacBeath and Schreiber, Science (2001); 289: 1760-1763.
Turk, et. al., Nature Biotechnology (2001); 19: 661-677.
Lebl and Krchnak, Methods in Enzymology (1997); 289: 336-392.

* cited by examiner

Primary Examiner—Leon B. Lankford, Jr.
Assistant Examiner—Susan Hanley

(57) ABSTRACT

Novel synthetic enzyme substrates, enhanced to have improved enzymatic specificity, are disclosed. These synthetic enzyme substrates consist of a substrate peptide that has had its specificity further improved by additional synthetic moieties, selected by combinatorial chemistry techniques, that act to sterically block non-target enzymes. These "steric restrictor" moieties may be labeled to produce a detectable signal upon enzymatic reaction. These novel substrates are particularly useful for improved enzyme substrate microarrays. Specific applications for improved protease substrate microarrays are discussed. A variety of applications for these improved protease substrate microarrays are also disclosed, including proteomics research, protease discovery, protease binding site characterization, diagnosis of the protease composition of biological samples, monitoring the angiogenic status of a tumor, monitoring the status of arthritis and other inflammatory diseases, and the discovery and optimization of novel drugs that modify or inhibit protease activity.

3 Claims, 10 Drawing Sheets

SYNTHETIC SUBSTRATE FOR HIGH SPECIFICITY ENZYMATIC ASSAYS

This application claims the priority benefit of provisional patent application 60/317,023 "Synthetic substrates for high specificity enzymatic assays", filed Sep. 4, 2001.

BACKGROUND OF THE INVENTION

Field of the Invention

The field of the invention is improved methods for screening and characterization of enzymes.

DESCRIPTION OF THE RELATED ART

Protease Assay Technology:

It has been estimated that 2% of the genome's gene products are proteases (Barret A. J., et. al., *Handbook of Proteolytic Enzymes* (1998), Academic London. Many biological processes, such as blood coagulation, angiogenesis, apoptosis; and many disease processes such as arthritis, cancer, and emphysema, are mediated by complex pathways involving multiple proteases. Thus a detailed knowledge of the proteases active in a given tissue is often of intense biological or medical interest. Drugs that inhibit or modify the activity of proteases are also of intense medical interest. Such drugs, such as HIV protease inhibitors, anti-cancer drugs, anti-microbial drugs, etc. are the subject of much research and development activity. Thus improved methods to streamline the development of novel protease inhibitors and modifiers are of intense interest to the pharmaceutical industry.

At present, protease assays are cumbersome. The present art is only capable of assaying a limited number of samples and protease types, and is poorly suited to analyzing samples that may contain multiple proteases with differing specificities. The present art is also poorly able to quickly screen a large number of potential protease binding sites in order to characterize a protease, or the effects of a protease inhibitory or modifying agent.

A good quote of the present state of the art can be found in U.S. Pat. No. 6,037,137, which states: "Clearly measurement of changes in the activity of specific proteases is clinically significant in the treatment and management of the underlying disease states. Proteases, however, are not easy to assay. Typical approaches include ELISA using antibodies that bind the protease or RIA using various labeled substrates. With their natural substrates assays are difficult to perform and expensive. With currently available synthetic substrates the assays are expensive, insensitive and nonselective. In addition, many "indicator" substrates require high quantities of protease which results, in part, in the self destruction of the protease."

Thus a major stumbling block is the insensitivity and non-selectivity of currently available synthetic substrates. This lack of sensitive and selective synthetic substrates has consequences that undermine progress in many areas of modern biology and medicine.

Often, biological samples of interest, such as plasma, and tissue biopsies, may contain a multiplicity of different proteases of different specificity. Often, these proteases may have a very short half-life. Often too, the different proteases may all serve as different components of a broader protease cascade or regulatory system. Important biological information will be lost if a sample is analyzed using slow techniques, techniques that require a large sample size, or techniques that can only partially analyze a sample's proteolytic activity.

Here too, present state of the art is inadequate. As is assessed by Harris et. al., *PNAS* 2000, 97(14), 7754-7759. "While several biological methods, such as peptides displayed on filamentous phage (2, 3), and chemical methods, such as support-bound combinatorial libraries (4), have been developed to identify proteolytic substrate specificity, few offer the ability to rapidly and continuously monitor proteolytic activity against complex mixtures of substrates in solution."

High-throughput screening methods for protease inhibitors or response modifiers are also hampered by current technology. Modern drug screening efforts typically produce many thousands of drug candidates, each of which may have an unknown effect on the activity and specificity of tens or hundreds of different proteases in the body. Each protease in turn may have specificity towards a multiplicity of different peptide targets, and a drug candidate can potentially alter this specificity. Using the present techniques, the analytical load quickly becomes overwhelming.

Ideally, what is needed is a high-throughput protease assay system that can almost instantly characterize the precise proteolytic activity of an unknown sample.

However due to the previously discussed problems of synthetic substrate insensitivity and non-selectivity, the overall technology of high-throughput protease assays has not advanced very far in recent years.

At present, the majority of the higher throughput protease assays are designed around the microplate or microwell format, typically using 96 well microtiter plates. For example, Intergen Corporation, Purchase New York, produces the Prochek™ universal protease assay kit. This consists of a custom plastic lid with 96 plastic pins, each pin having a different fluorescent protease substrate bound to its tip. The lid is placed over a 96-well microtiter plate, with samples in each well of the plate. Samples with proteolytic activity will cleave the fluorescent substrate and the resulting liquid sample in the well will become fluorescent. Because the labeled peptides are mounted on pins, each pin being several millimeters long, relatively large amounts of sample (typically several milliliters or more) are required for each assay. The system is only capable of monitoring a relatively small (96 samples or less) number of different protease substrates per device.

This makes the system impractical for the high-throughput microscale studies often required for modern biomedical analysis.

Rano, et. al. *A combinatorial approach for determining protease specificities: application to interleukin-1B converting enzyme (ICE) Chem Biol* 1997 February; 4(2): 149-55), and Harris et. al., *Rapid and general profiling of protease specificity by using combinatorial fluorogenic substrate libraries PNAS* 2000, 97(14) 7754-7759 teach ways to improve the efficiency of microtiter plate techniques by putting multiple protease substrates in each 96 well microtiter plate, and using different combinations of these mixtures to deduce which protease substrate is the likely protease target.

A number of companies produce protease assay system reagent kits adapted to the 96 well microwell plate format, including Chromagen corporation, San Diego, Calif.; Chemcon International of Temecula Calif., BioMol Research laboratories, and others.

U.S. Pat. No. 5,580,747 teaches a protease assay using protease substrates consisting of charged, dye-linked, peptides. A protease is applied to the substrate and the reaction products separated by gel electrophoresis. This technology is commercially available as the PepTag™ protease assay, produced by Promega Corporation of Madison Wis.

Lam and Lebl "*Synthesis of a one-bead one-compound combinatorial peptide library*", *Methods Mol Biol* 1998; 87:1-6) teach combinatorial peptide libraries on the microbead format.

U.S. Pat. No. 5,741,659 teaches a rapid microbial protease assay in which microorganisms (containing protease enzymes) are immobilized to a filter support, and the proteolytic activity of the microorganisms probed by chromogenic peptide substrates.

U.S. Pat. No. 5,418,143 teaches a bibulous membrane containing a single fluorescent substrate that is not tightly bound to the membrane. Such systems are suitable for characterizing levels of single proteases, but are unsuited for high-throughput analysis of multiple proteases. Because the membrane is bibulous and because the fluorescent substrate is unbound, rapid diffusion occurs when a sample is applied to the membrane. The bibulous membrane structure acts to spread applied samples, which impedes the formation of small spots where individual protease substrates can be localized and analyzed.

Angiogenesis Assays:

Angiogenesis, the process of tissue vascularization, is now a major focus of medical research with applications for cancer (inhibition of tumor vascularization), heart disease (promotion of the revascularization of ischemic cardiac tissue), and many other medical areas. It is now known that blood vessels respond to a variety of angiogenic signals put out by tumor and other tissue, and that proteases or proteolytic fragments of common tissue proteins are the source of many of these different angiogenic signals (either pro-angiogenic or anti-angiogenic). Thus an ability to precisely characterize the proteolytic status of a complex biological sample derived from, for example, a tumor biopsy, is of high interest to modem medical research. Here however, current protease characterization technology is lacking. As summarized in a recent review article by J. Folkman, et. al. *Angiogenesis Research: Guidelines for Translation to Clinical Application* (2001) *Thromb Haemost* 2001, 86:23-33

" . . . the dose of an angiogenesis inhibitor is best titrated against the total angiogenic output of a tumor. Angiogenic output can be defined operationally as the sum total of angiogenic activity from positive regulators of antiogenesis released by a tumor (e.g. bFGF, VEGF, IL-8, etc.) minus the antiangiogenic activity due to negative regulators of angiogenesis generated by a tumor (e.g. thrombospondin, angiostatin, endostatin, etc.) (23-26). The angiogenic output of a primary tumor may differ from that of its metastases and may also differ among tumors of the same type, e.g. breast cancers . . . . However, an urgent challenge for future angiogenesis research is to develop an assay based on a simple blood or urine test that could quantify the total angiogenic output of a patient's tumor or tumor burden. In the absence of a method to quantify angiogenic output, titration of dosing for an angiogenesis inhibitor is difficult, not unlike administering insulin without a blood glucose test or coumadin without a prothrombin test."

Synthetic Peptide Synthesis Technology:

Enzymatic substrate peptides, suitable as substrates for proteases or other enzymes, may be created in a number of ways. Typically various combinatorial chemistry techniques, such as solid phase peptide synthesis, are used.

A number of combinatorial solid phase peptide syntheses may be used to produce synthetic peptides. A good review of the more popular solid phase peptide synthesis methods can be found in Chan and White, *Fmoc Solid Phase Peptide Synthesis, a practical approach* (2000), Oxford University Press, Oxford UK., the contents of which are incorporated herein by reference Technology for Detecting Protease Activity:

One of the more popular protease detection methods is the use of fluorescence resonance energy transfer between a donor fluorophore at one end of a peptide chain, and a quencher at the other end of the peptide chain. These methods were reviewed by Knight "*Fluorimetric assays of proteolytic enzymes,*" *Methods in Enzymol.* (1995) 248:18-34.), the contents of which are incorporated herein by reference. Here, proteolytic cleavage of the peptide link connecting the fluorophore and quencher liberates the quencher to diffuse away from the fluorophore. This results in an increase in fluorescence.

A variation on this quencher method is taught by U.S. Pat. Nos. 5,605,809 and 6,037,137. This variation brings a first fluorophore in close proximity to a second fluorophore via a folded peptide backbone. This technique has the advantage that the protease cleavage site need not be immediately adjacent to either of the fluorophores. However it has the disadvantage that to avoid disrupting the folded structure, the length of the protease cleavage site should ideally fall between 2-15 amino acid residues in length.

Another very popular method is the use of peptide-quenched fluorescent moieties, such as the 7-amino-4-methylcoumarin (AMC) fluorophore, the 7-amino-4-carbamoylmethylcoumarin fluorophore (Harris, et. al. *PNAS* 97 (14) 7754-7759 (2000)), or the peptide quenched Rhodamine 110 fluorophore (Mangel et. al., U.S. Pat. No. 4,557,862). Here the intrinsic fluorescence of a fluorophore is quenched by one or more covalently linked peptides, and the fluorescence is restored upon cleavage of the peptide.

Although the Rhodamine 110 molecule operates with high efficiency, uses visible light for excitation and emission, and is otherwise an excellent label for fluorescence based protease assays, it has a few drawbacks that limit its use. The Rhodamine 110 molecule is divalent and normally incorporates two peptides of identical sequence, with both "N" terminal peptide groups exposed. This has the drawback that peptides with this polarity can not be incorporated into the interior of a larger peptide chain. Thus this label has primarily been used for protease substrate assays where the Rhodamine 110 molecule effectively represents the final "C" terminal group on the substrate.

Variations on Rhodamine 110 molecule methods, suitable for Caspase assays, are taught by U.S. Pat. No. 6,248,904.

Methods of linking fluorescent peptides to insoluble polymers and solid phase supports are taught by U.S. Pat. No. 4,897,444 and PCT patent application WO 01/10890 A3.

Luminescent labels are taught by U.S. Pat. No. 4,748,116.

A good review of cross-linker molecules and cross-linking techniques is given by Baumert and Fascold, *Methods in Enzymology* (1989), 172, 584-607.

Protease inhibitor technology: Non-peptide groups can also be used to probe the active sites of proteases. For example, Groutas, et. al., teach the use of functionalized sulfonamides, coupled to a 1,2,5-thiadiazolidin-3-one 1,1 dioxide scaffold, as a design and diversity element to improve the specificity of protease inhibitors against specific serine proteases (Groutas et. al., *Bioorg Med Chem* 2001 June; 9(6):1543-1548).

Microarray Technology:

Microarray methods have become widely used for nucleic acid research, and a large number of nucleic acid microarrays are commercially available from Affymetrix Inc., Incyte Pharmaceuticals, Inc., and many other companies. These methods (reviewed in Schena, *Microarray Biochip Technology* (2000) Eaton Publishing, Natick. Mass.) generally work by binding a large number of nucleic acid microsamples to the surface of a flat support. Samples containing one or more unknown complementary nucleic acids are then exposed to the nucleic acid microarray, and the sample is allowed to hybridize to the microarray. Hybridized nucleic acids are then detected by various means, and the overall nucleic acid composition of the unknown sample is assessed.

U.S. Pat. No. 5,143,854 teaches photolithographic methods to construct polypeptide microarrays for receptor binding assays.

In contrast to the intense research and commercial activity currently ongoing with nucleic acid microarrays, and the equally intense modern interest in proteomics, there is comparatively little research or commercial activity of any sort with enzymatic substrate microarrays, particularly protease substrate microarrays. This is because enzymatic substrate microarrays pose a number of major technical challenges. Nucleic acid microarrays are built up using biological polymers consisting of only four basic nucleic acid components. The detection of positively reacting array elements is easy to assay, using nucleic acid hybridization methods. Modifying the chain length of the nucleic acid can easily control the reaction specificity. The simplicity of nucleic acid microarrays lends itself to the construction of complex arrays using photochemical methods.

By contrast, enzyme substrate microarrays are much more complex. For example, if the enzyme substrate is a peptide, it must be constructed using 20 or more amino acid components, rather than four nucleic acid components. Thus array construction by photochemical methods requires many steps, making it difficult to construct large arrays with long synthetic peptides. Enzymatic activity is often harder to detect, and if the non-steric restricted synthetic peptide substrates of the prior art are used, there are major sensitivity and selectivity problems.

As a result, previous peptide microarrays have been constructed primarily to demonstrate that simplified binding assays are possible, rather than being constructed for any practical purpose.

Use of peptide microarrays, constructed by photochemical methods, for antibody recognition of peptide patterns was taught by Fodor et. al., *Science* 1991, 251, 767-773. Use of peptide microarrays for protein kinase or protein-protein binding was taught by MacBeath and Schreiber, *Science* 2000, 289, 1760-1763. Here glass slides were chemically activated to covalently bind peptides, and various peptides were spotted onto the slides using conventional spotting equipment. The peptides formed a covalent bond with the derivitized glass. Falsey, Renil et al, taught an extension of this use of peptide microarrays for cell adhesion assays in *Bioconjugate Chem.* 2001, 12, 346-353.

Alternative methods to attach peptides to solid supports are taught by U.S. Pat. No. 6,150,153, which teaches the use of polyethyleneimine layers to facilitate peptide linkages. U.S. Pat. No. 4,762,881 teaches the use of incorporating an artificial benzoylphenylalanine into a peptide and allowing the peptide to attach to a solid substrate having an active hydrogen (such as polystyrene) using ultraviolet light. U.S. Pat. No. 4,681,870 teaches methods for derrivitizing silica surfaces to introduce amino or carboxyl groups, and then coupling proteins to these groups.

U.S. Pat. Nos. 5,527,681 and 5,679,773 teach methods for immobilized polymer synthesis and display suitable for microarrays, and various fluorescent-labeling methods to detect proteolytic cleavage. At present, there are no commercially available protease substrate microarrays based upon the art of these patents.

Synthetic protease substrates of the prior art tend to react nonspecifically with non-target proteases. For example, see Turk et. al., *Nature Biotechnology* (2001) 19, 661-677. In this work, a large number of different matrix metalloprotease cleavage site peptide motifs were generated by peptide library techniques. This library of short peptide motifs (each peptide being 8 amino acids long, with, 4 amino acid residues before the scissile group, and 4 amino acid residues after the scissile group) was challenged with an array of different matrix metalloproteases. Even though this synthetic peptide library was highly selected to optimize specificity, the results showed a large amount of "cross-talk" between the different proteases and peptide protease targets. That is, matrix metalloprotease (a), although having the highest activity against its own optimized protease target (a) nonetheless may have more cross-talk activity against the optimized peptide target (b) for matrix metalloprotease (b), than matrix metalloprotease (b) has for its own optimized peptide target (b). Thus if these particular synthetic peptide targets (a, b) were incorporated into a protease microarray designed to characterize a biological sample for the presence of matrix metalloproteases (a and b), this microarray, using the insensitive and nonselective synthetic peptide substrates of the prior art, would have limited utility in discriminating between biological samples containing matrix metalloproteases (a and b), or samples containing just matrix metalloprotease (a).

As previously discussed, it is likely that synthetic substrate specificity problems have been the one of the key technological reasons why no successful enzyme microarrays, and in particular, no successful protease substrate microarrays, have been commercialized. The ability to discriminate between different proteases and different protease targets is low, and the unwanted background of non-specific reactions is too high.

SUMMARY OF THE INVENTION

As previously discussed, a significant drawback of protease substrate microarrays of the prior art, which were based upon short (e.g. roughly 10 amino acids or less) synthetic peptide sequences, is lack of specificity. In the native state, when a protease peptide substrate is part of a larger protein, a protease specific to a peptide substrate on a target "A" protein is typically restricted from gaining access to a similar protease peptide substrate on a non-target "B" protein, due to steric constraints. On the native protein containing the peptide substrate, amino acid residues that are distant from the protease site can fold back and act to restrict access to the "wrong" proteases. By contrast, when short synthetic peptides are used, the short synthetic peptide can readily enter the active site of many different proteases, and be cleaved. As a result, when a microarray consisting of a mix of synthetic peptides of the prior art is challenged with one or more proteases, lack of specificity can result, and a confusing reaction pattern can ensue. In the case where a mixture of proteases is analyzed using the microarrays of the prior art, a protease that normally would have restricted specificity, due to steric constraints imposed by its native targets, is now able to cleave a broad range of peptides, resulting in a high noise background. This can obscure the signals due to other proteases in the sample.

In addition to proteases and protease substrates, this problem also occurs with short synthetic peptides that act as substrates for non-proteolytic enzymes and enzyme assays as well (kinases, glycosylases, etc.).

Thus to produce protease substrate microarrays with enhanced utility for research, drug screening, and diagnostic applications, it is important that the substrate array attempt to present not only the actual binding site of the native substrate, but also present additional information that conveys more of the steric constraints of the native substrate structure.

One way to do this is to use a labeled version of the native protease substrate. Such labeled versions can be constructed by, for example, cleaving a native substrate with the target protease, purifying the two cleavage products, labeling one or both of the cleaved products, followed by a ligation step to reassemble the native substrate. Such a process is labor intensive, however, and tends to discourage the creation of protease substrate arrays with a large number of array elements.

Definition of peptide substrate: Here, the term "peptide substrate" is used to denote a typically short (roughly 10 amino acid length or less) peptide region that fits into the active site of the enzyme, is of sufficient length to be acted upon by the enzyme (e.g. is cleaved for a protease, phosphoralated for a kinase, etc.) and that by itself demonstrates some degree of enzymatic specificity (e.g. preferential reaction with certain members of an enzymatic class over other members of the same class).

Although prior art did attach synthetic peptide substrates to a variety of other moieties for a variety of reasons, there was no systematic effort to rationally design or select such moieties to optimize enzymatic sensitivity and selectivity.

The present invention discloses the utility of systematically enhancing the sensitivity and specificity of synthetic peptide substrates by use of synthetic "steric restrictors". In one embodiment, the invention consists of a systematic set of methods to create a library of larger artificial molecules that convey additional steric constraints, and that can be covalently attached to one or both ends of the peptide substrate. By preparing and screening a sufficiently large enough library of such artificial steric restrictors, conditions mimicking the natural steric constraints of the native peptide substrate, in its native host protein, can be created. An additional advantage of artificial steric restrictors is that they can be usefully employed in combinatorial chemistry synthetic procedures, leading to the creation of enzyme substrate arrays with a very large number of array elements.

Definition of a steric restrictor: Here, the term "steric restrictor" is used to denote a synthetic molecule or moiety that does not fit into the active site of a protease or other enzyme. Rather, the steric restrictor interacts with enzymatic regions outside the enzyme's active site, and may act to block enzymatic access to the peptide substrate, or alternately modify the conformation of the enzyme so as to facilitate enzymatic access to the peptide substrate. In this definition, although a steric restrictor may have the additional properties of serving as a terminal cap for protection against exoproteases, or as a label group that generates a detectable signal upon proteolytic cleavage, or as a binding group that binds the peptide to a solid phase, etc., these properties alone are not necessary or sufficient to define a steric restrictor. Rather, for purposes of this art, a steric restrictor must convey additional specificity to the substrate (e.g. accentuate the differences between reactivity with two different enzymes of the same class) independent of any exoprotease blocking activity, label activity, or binding function.

As an example, amino acids naturally occur in the 1-amino acid enantiomer, and enzymes are typically unable to react with substrates constructed of d-amino acid enantiomers. Prior art, e.g. U.S. Pat. No. 4,247,454, has used this fact to create synthetic peptides resistant to exopeptidase degradation by use of a single d-amino acid placed on the amino terminal of a protease substrate. Here, however, this use of a single d-amino acid would not be considered to fall within the definition of "steric restrictor" of this art, because the steric restriction activity is not independent of the exopeptidase blocking activity. Here the d-amino acid cap is intended to fit inside the active site of an enzyme and block enzymatic activity, rather than sterically prevent enzymatic access to the peptide.

However, using the present definition of steric restrictors, a longer peptide segment composed of two or more d-amino acids would be considered a steric restrictor if the sequence of the longer d-amino acid peptide segment was chosen to specifically enhance the peptide's enzymatic specificity for one endopeptidase over another.

Similarly, a label moiety, such as a chromophore or fluorophore placed on the carboxyl terminal of a protease substrate, would not be considered a steric restrictor because the steric restriction activity is not independent of the labeling activity of the labeled moiety. However a labeled moiety with additional side groups, where these side groups do not contribute to the function of the labeled moiety in generating a detectable signal, but rather where these side groups were selected for their ability to enhance enzymatic specificity, would be considered to be a steric restrictor.

Similarly a crosslinking moiety, such as a long chain polymer, that crosslinks a substrate peptide to a solid phase support, would not be considered a steric restrictor because the steric restriction activity is not independent of the binding activity of the crosslinking moiety. However a crosslinking moiety, with additional side groups, where these side groups do not contribute to the ability of the crosslinking moiety to crosslink the peptide, but rather where these side groups were selected to specifically enhance enzymatic specificity, would be considered a steric restrictor. Thus a cross-linking peptide might well fall within the definition of "steric restrictor" of this art if the amino acid composition and sequence of the peptide were chosen to enhance enzymatic specificity, rather than for their cross-linking capability.

Synthetic peptide substrates with specificity enhanced by steric restrictors (SR-peptides) are useful for a variety of different enzymatic assays, including various solution phase assays. In addition, they are particularly well suited for enzyme substrate microarrays and, in particular, the high-specificity protease substrate microarrays discussed in some detail in this document.

Novel fluorogenic probes for such synthetic SR-peptides are also disclosed.

In the broadest aspect, the high specificity protease substrate microarrays disclosed herein consist of an addressable array of different SR-peptides, tightly bound to a solid support. The SR-peptides need not be covalently bound to the solid support, but should be bound tightly enough so as to maintain their positional location for the duration of the assay when exposed to a liquid sample medium. The SR-peptides further contain labeled moieties (typically in the steric restrictor portions) so that upon proteolytic cleavage of the substrate portion of the SR-peptide, the presence or absence of the peptides's specific proteolytic cleavage generates a detectable signal. The array is "addressable" in that the sequence of any given SR-peptide can be determined by correlating its two dimensional position on the array with a previously determined table of peptide address locations.

Preferably the peptides are bound to the solid support in a way that helps preserve the proteolytic susceptibility of the SR-peptide in question. Preferably the peptide substrate portion of the SR-peptides are chosen from the group of known protease binding sites, or suspected protease binding sites. Preferably a multiplicity of SR-peptides with different sequences are arranged in a high density array of spots so as to enable the simultaneous assay of tens, hundreds or thousands of different protease targets, or suspected protease targets, with one application of a single, small volume, sample.

Reading technology for such protease substrate microarrays is also disclosed. These methods include fluorescence, chromogenic, or luminescence microscopy or scanner methods, as well as various electrochemical detection methods.

Applications for such protease substrate microarrays are also disclosed. These applications include analysis of complex protease mixtures from biological or medical samples, angiogenesis status assays, identification of novel protease inhibitors or response modifiers, discovery of novel proteases, and high throughput discovery of novel protease inhibitor or allosteric modifier drugs.

Although throughout this document, protease assays and protease substrates are used as the primary examples, it should be understood that the improved synthetic substrates and microarray methods taught herein can be applied to a variety of other different classes of enzymes as well.

DETAILED DESCRIPTION OF THE INVENTION

Figure 1:
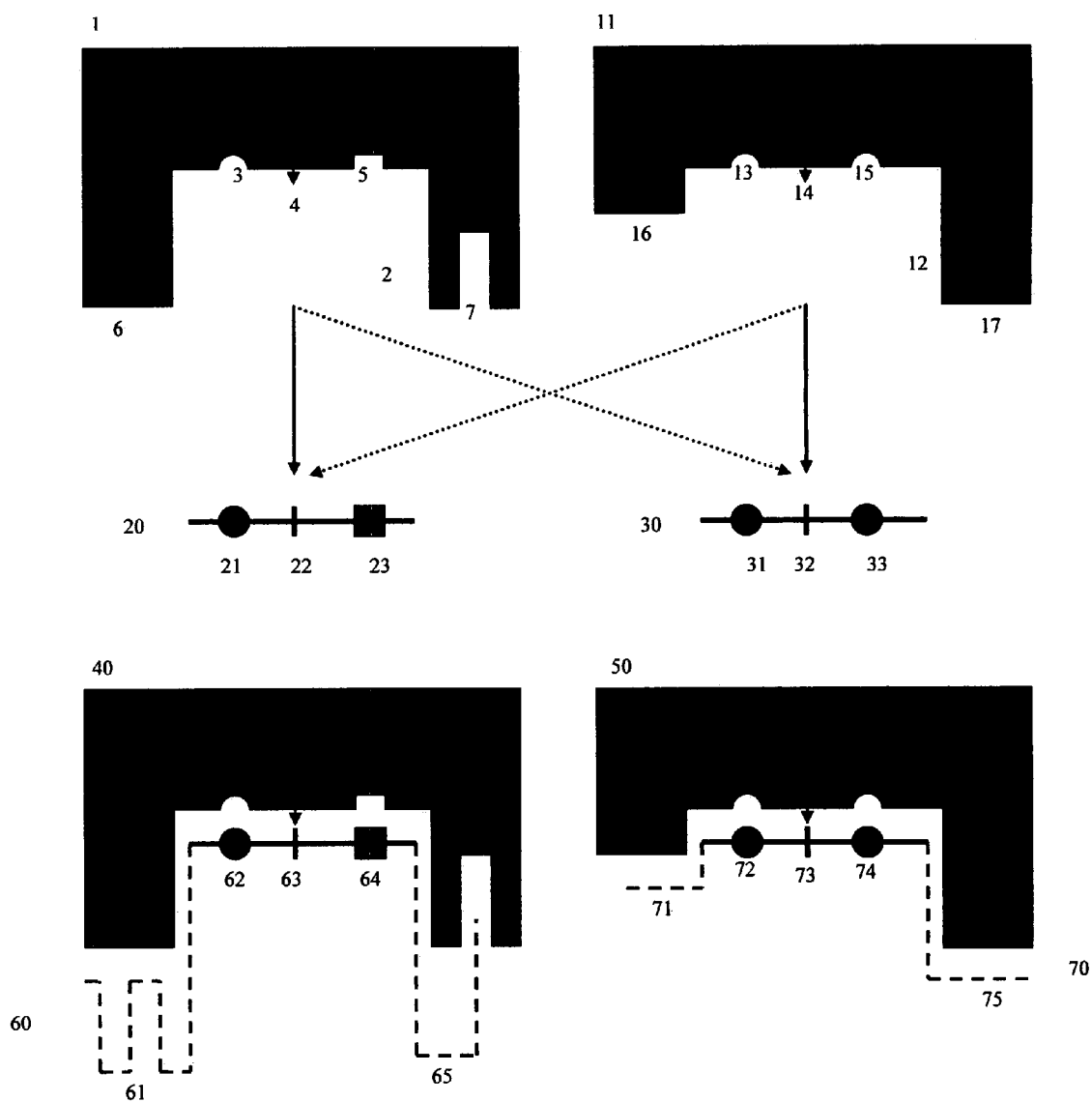
FIG. 1 shows a diagram of how steric restrictor groups function
Figure 2:
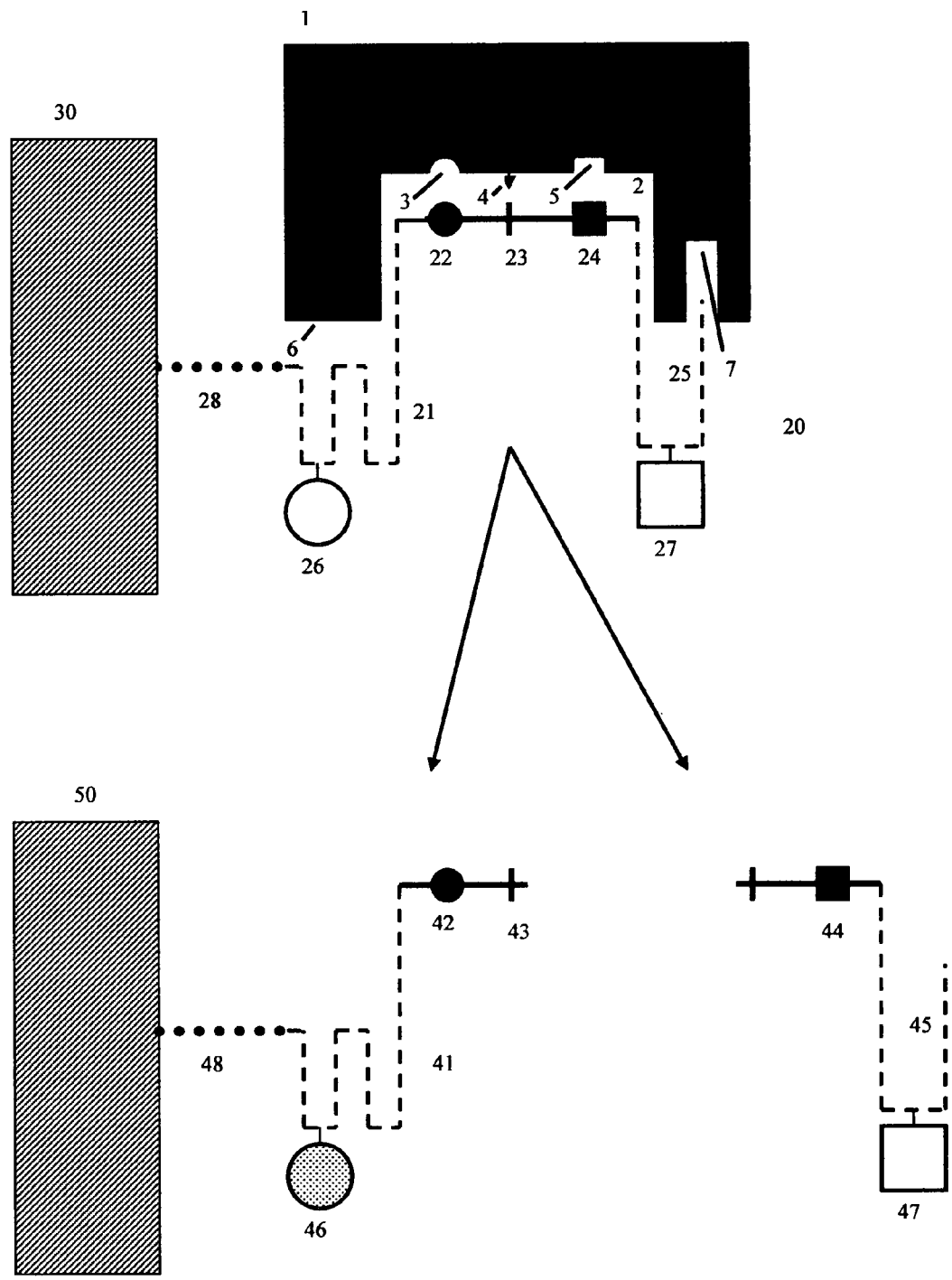
FIG. 2 shows a protease substrate peptide flanked with a steric restrictor group containing a fluorescent label on one end, and a different steric restrictor group containing a fluorescence quencher moiety on the other end.

FIGS. 1 and 2 show a detailed schematic of steric restrictor function using protease (proteolytic) enzymes and protease substrates as an example:

FIG. 1 shows two different protease enzymes (1, 11) reacting with two different peptide substrates (20, 30). Here protease (1) has an active site (2), which contains amino acid residues (3) and (5) which bind to complementary groups (21, 23) on peptide substrate (20), as well as a site (4) that cleaves a scissile site (22) on peptide substrate (20). Similarly, protease enzyme (11) has an active site (12), which contains amino acid residues (13, 15) that bind to complementary groups (31, 33) on alternate peptide substrate (30). Protease enzyme (11) also has its own site (14) that cleaves a scissile site (32) on alternate peptide substrate (30). Protease (1) also has additional regions (6, 7) that do not participate in the enzymatic reaction with substrate (20) because substrate (20) contains no additional groups to interact with regions (6, 7). Likewise protease (11) has its own distinct additional regions (16, 17) that do not participate in the enzymatic reaction with its own substrate (30) because substrate (30) contains no additional groups to interact with regions (16, 17).

Note that although the active site (2) of enzyme (1) contains amino acid residues (3, 5) with preferential binding activity to the complementary groups (21, 22) on substrate (20), and thus reacts preferentially with substrate (20), alternate substrate (30) is still able to enter the active site (2) of enzyme (1) and, by assuming many different steric configurations inside active site (2), occasionally position scissile site (32) so that it may be cleaved by site (4) on enzyme (1). Similarly, although the active site (12) of enzyme (11) contains amino acid residues (13, 15) with binding activity to the complementary groups (31, 33) on substrate (30), and thus reacts preferentially with substrate (30), alternate substrate (20) is still able to enter the active site (12) of enzyme (11) and, by assuming many different steric configurations inside active site (12), occasionally position scissile site (22) so that it may be cleaved by active site (14) on enzyme (11). Thus due to lack of additional steric restriction, there is some cross talk between the two enzymes and the two substrates.

However if peptide substrate (20) is modified to additionally contain steric restrictor groups (61, 65), complementary to regions (6, 7) on enzyme (1) forming a new substrate (60); specificity for enzyme (1) can be improved. Similarly if substrate (30) is modified to additionally contain steric restrictor groups (71, 75) complementary to regions (16, 17) on enzyme (11), forming a new substrate (70); specificity for enzyme (11) can also be improved.

The reaction between modified substrate (60) and enzyme (1) (which is now designated enzyme (40) to distinguish this reaction from the earlier reaction) has higher specificity for enzyme (1, 40) over enzyme (11, 50) because the steric restrictor groups (61, 65) on the substrate are complementary to the regions (6, 7) on enzyme (1, 40), but not complementary to the regions (16, 17) on enzyme (11, 50). Thus substrate (60) is unable to enter the active site on enzyme (11, 50), and thus can not react. By contrast, substrate (60) can enter the active site of enzyme (1, 40) and present the substrate's complementary groups (62, 64) and scissile site (63) to the proper groups on enzyme (1, 40).

Similarly the reaction between modified substrate (70) and enzyme (11) (which is now designated enzyme (50) to distinguish this reaction from the earlier reaction) has higher specificity for enzyme (11, 50) over enzyme (1, 40) because the steric restrictor groups (71, 75) on the substrate are complementary to the regions (16, 17) on enzyme (11, 50), but not complementary to the regions (6, 7) on enzyme (1, 40). By contrast, substrate (70) can enter the active site of enzyme (11, 50) and present the substrate's complementary groups (72, 74) and scissile site (73) to the proper groups on enzyme (11, 50).

Label moieties may be affixed to steric restrictors in order to facilitate the detection of enzymatic activity. Here, the label moieties reviewed by Knight, (*Methods in Enzymol.* (1995) 248:18-34.) may be used. An example of the use of such labels, again using proteases and protease substrates as an example, is shown in FIG. 2.

FIG. 2 shows a protease substrate peptide (20) flanked with a steric restrictor group (21) containing a fluorescent label (26) on one end, and a different steric restrictor group (25) containing a fluorescence quencher moiety (27) on the other end. In this example, the protease substrate (20) is bound to a solid support (30) by a linker moiety (28).

Substrate peptide (20) interacts with protease enzyme (1) through its peptide substrate group (22, 23, 24) that fits into active site (2) of enzyme (1). This peptide substrate group is able to fit into the active site (2) of enzyme (1) because the steric restrictor groups (21, 25) of the substrate peptide (20) are complementary to regions (6, 7) on enzyme (1). Here the binding site (2) of protease (1) recognizes the complementary groups (22, 24) on the substrate region of peptide (20) by amino acid residues (3, 5), and is able to cleave the scissile site (23) on peptide (20) by its site (4).

After the protease enzyme cleaves scissile group (23), the two halves of peptide (20) are free to separate. One portion remains bound to solid support (50), and one portion is free to move away from the solid support. In particular, the portion consisting of the linker (48), fluorescent label (46), steric restrictor group (41) and a portion of the peptide substrate region (42) remain bound. The fluorescence of label (46) is no longer quenched by the quencher moiety (47), and thus the proteolytic cleavage event can be monitored.

Note that in combinatorial selection methods, where the sequences of steric restrictor groups (41, 45) are not known in advance, the sequence of steric restrictor group (41) could be determined by obtaining the solid phase support and sequencing the bound peptide after cleavage. Similarly, steric restrictor group (45) could be determined by binding the solution phase steric restrictor group (45) by an affinity purification method (for example by a solid phase bound antibody against the quencher moiety, etc.), and sequencing this peptide.

Steric Restrictor Creation Techniques:

In the following example, proteases, protease substrate peptides, and fluorescent labels that detect proteolytic cleavage will be used. Note however that the following methods may be used for other enzymatic types and detection modalities (such as kinases, kinase substrate peptides and detection of phosphorylation using radioactive $P^{32}$, or glycosylation enzymes, glycosylation substrate peptides, and detection of glycosylation, etc.) as well.

Artificial steric restrictors can be developed by a number of methods. One of the simplest methods is to synthesize them from amino acids using combinatorial chemistry techniques. (Here, the methods described by Lebl and Krchnak, *Synthetic Peptide Libraries, Methods in Enzymology* (1997) 289, p 336-392, the contents of which are incorporated herein by reference, may be used) For example, a population of peptide synthesis beads can be split into subpopulations and derivitized with many different combinations of amino acids. After a first round of synthesis, the beads may again be randomized and each subjected to peptide chain extension using a second combination of amino acids, and so on. After a number of rounds of synthesis (typically 5-25 rounds), a bead library containing a variable set of steric restrictor peptide groups, one different group for each bead, is generated.

This bead library of variable steric restrictor groups can then be pooled, and have a constant enzymatic substrate group covalently attached to the variable steric restrictor group by several rounds (typically 3-10 rounds) of continued amino acid extensions of the peptide chain.

Finally, this bead library consisting of many thousands or millions of beads, each with a unique steric restrictor group, but each with the same enzymatic substrate group, may once again be split into subpopulations, and a second combinatorial round of peptide synthesis by amino acid chain extension (typically 5-25 rounds) may be done. This will produce a bead library, where each bead contains a first variable set of steric restrictors, a constant enzymatic substrate group, and a second variable set of steric restrictors.

Typically the first steric restrictor will be about 5-25 amino acid residues in length, the constant enzymatic substrate will be about 3-10 amino acid residues in length, and the second steric restrictor will be about 5-25 amino acids in length. In some cases, a synthetic substrate will contain only one steric restrictor, which may be on either the "N" or "C" terminal side of the enzymatic substrate peptide.

The first steric restrictor may contain a label that provides a detectable signal, such as a fluorescent moiety. The second steric restrictor may contain a second moiety, such as a fluorescence quencher moiety, that acts to quench the fluorescence (or other detectable signal) of the first label.

Continuing with the use of proteases as an example, once a library of beads containing many alternative steric restrictors is developed, the library may then be challenged with a mixture of non-target proteases. That is, the bead mixture will first be digested with proteases where steric blockage is desired. The bead mixture will then be sorted and fluorescent beads (indicating non-specific protease activity) will be discarded. The remaining non-fluorescent beads (indicating steric blockage to non-specific protease activity) will then be challenged with the target protease. Those beads that subsequently become fluorescent will typically retain the solid phase bound steric restrictor. These beads may then be subjected to microsequencing analysis and the amino acid composition of the first steric restrictor may be ascertained. Alternatively or additionally, the cleaved non-solid phase restrictor may be retrieved from the liquid phase by capture of a labeled moiety, such as a biotin label. This second cleaved restrictor peptide sequence may also be ascertained by microsequencing analysis.

In this way, a library of steric restrictor sequences that convey additional specificity to various peptide protease substrates may be developed. Normally, it is expected that each protease substrate target sequence will have its own semi-unique set of steric restrictors. However there may be situations, such as screening for unknown or new proteases, where it is advantageous to construct a less optimized but more general set of steric restrictors, and use these general restrictors with a wider variety of different protease target peptides.

Generic steric restrictors may be created by methods similar to those used to produce specific steric restrictors. Here, it is preferable to use larger beads, or larger substrate units for solid phase peptide synthesis (T-bags, etc.), that may be subdivided into smaller subunits. The first digestion with non-target proteases should not contain any proteases from the generic class.

The candidate beads or solid phase synthesis substrates from the first digestion step will then be subdivided into multiple subunits, with one subunit retained for later sequencing. The other subunits will be challenged by exposing each subunit to a different protease cocktail. Here, each different protease cocktail will contain a different set of proteases from the full generic protease set. Retained portions, from those beads that show positive reaction with multiple cocktails, will then be sequenced. More candidate steric restrictor groups with these sequences will then be synthesized, and further characterized as to their relative suitability for use as generic steric restrictors.

Figure 3:
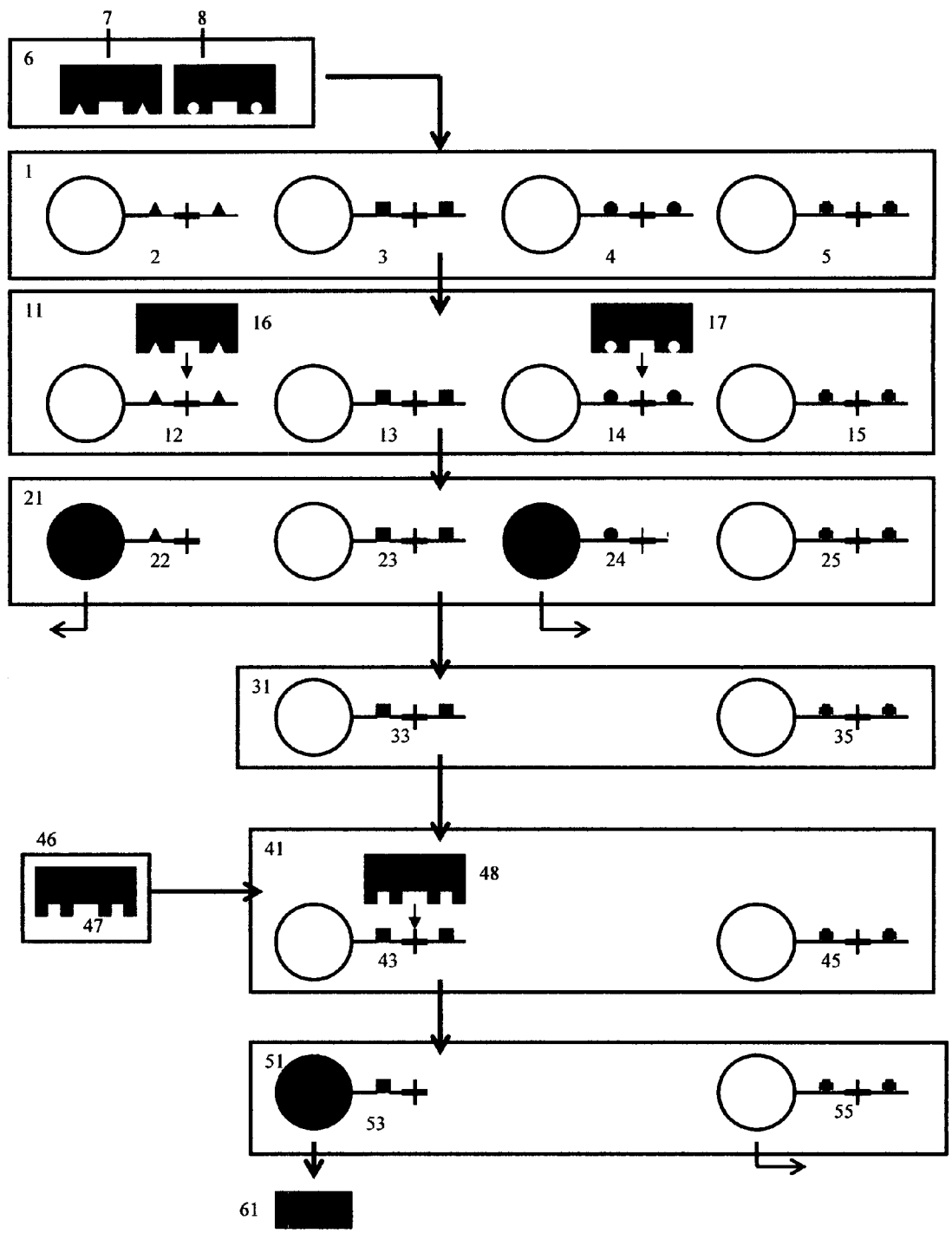
FIG. 3 shows a scheme by which steric restrictor groups may be created and selected

FIG. 3 shows a scheme by which steric restrictor groups may be created and selected, in more detail. Again, proteases and protease substrates are used in this example.

In this example, a large array of different microbeads (1), each bead containing a different set of peptide steric restrictors (2, 3, 4, 5), but normally each containing the same protease substrate region, is constructed by combinatorial solid phase peptide synthesis techniques. The steric restrictor groups additionally have label moieties that enable proteolytic cleavage of the protease substrate region to be detected. Typically millions of different steric restrictor peptides will be constructed for (1). Often, these will be constructed using d-amino acids for the steric restrictor regions, and l-amino acids for the protease substrate region.

To select for those steric restrictors that convey resistance to non-target proteases to the protease substrate (enzymatic substrate) region, the beads (1) are exposed to a mixture of enzymes (6) containing a variety of different non-target proteases (7,8). Protease digestion is allowed to commence (11). During this digestion, non-target proteases (16, 17) cleave the protease substrates on the beads that are linked to steric restrictor groups (12, 14) that are permissive for the non-target proteases. By contrast, beads containing steric restrictor groups (13, 15) that are not permissive for the non-target proteases do not have their protease substrate groups cleaved.

After the digestion reaction is finished (21), those beads susceptible to cleavage by the non-target proteases (22, 24) produce a detectable signal, usually by the activation of a fluorescent moiety that was quenched when the substrate peptide was attached. By contrast, the beads resistant to non-target protease attack produce either no signal, or a different detectable signal. The beads are sorted and the beads (22, 24) showing a positive reaction signal (usually fluorescence) are removed from the bead population.

The remaining unreacted beads (31) are washed, and then subjected to a second digestion, this time using an enzyme mixture (46) containing the target protease (47) or proteases. Here those beads containing steric restrictor groups that were non-permissive to non-target protease, but are permissive to the target protease or proteases (43), react with the target protease mix. By contrast, those beads that contain steric restrictor groups that are non-permissive to both the non-target proteases and the target proteases (45) remain unreactive.

The beads are again washed (51) and separated into signal positive (53) and signal negative (55) groups. The sequence of the steric restrictor peptides bound to the signal positive beads is determined by microsequencing techniques (61). If the sequence of the steric restrictor peptides liberated from the peptide by the cleavage reaction is desired, step 41 may be done with the beads digested in individual microwells. The soluble peptides containing the liberated steric restrictor peptides may then be isolated by affinity methods, and also determined by microsequencing. Alternatively, a second population of beads with the polarity of the peptide reversed may be prepared, and the other steric restrictor will then appear on the reaction products remaining bound to the bead.

For ease of illustration, each bead is shown with two identical steric restrictor groups, however it should be understood that this is not the typical situation. Typically, each bead will have either two non-identical steric restrictor groups, or else one steric restrictor group, which may be located on either the bead side or the free side of the peptide substrate.

A wide variety of amino acids or other monomer units may be used to construct the steric restrictor sequences. Amino acids or amino acid variants can consist of the natural 1-amino acids, or unnatural synthetic amino acids. In order to avoid unwanted side-reactions (e.g. unwanted proteolytic cleavage of the steric restrictors, etc.) it is helpful (although not essential) to construct the steric restrictors out of molecules that will not themselves be altered by the enzymes present in the applied sample.

There are a number of ways to do this. One particularly good way is to use artificial amino acids that do not tend to react with naturally occurring enzymes. These may include fluorinated amino acids, and amino acids with non-natural side groups. Artificial d-amino acids are particularly advantageous, as they are resistant to proteases, and may be easily combined in millions of different possible steric restrictor groups using standard combinatorial protein synthesis techniques.

Alternatively, non-peptide steric restrictors may be used. Almost any family of molecular entities may be used for this purpose, provided that the family of molecular entities lends itself to the creation of large numbers of alternate structures by combinatorial chemistry techniques. Alternative steric restrictors may be constructed from sugars, polysaccharides, nucleic acids, plastic monomers, and other polymeric macromolecules.

Although the screening of large steric restrictor libraries (generated by combinatorial chemical methods) is often the most feasible way to design steric restrictors, steric restrictors may also be designed by computer modeling methods. For example, if the conformation of the native proteolytic target is known, steric restrictors may be designed with the aim of reproducing the broader steric environment conformation of the native active target.

The two methods are not mutually exclusive. For example, the output from computer modeling studies may be used to help narrow down certain preferred structures for further combinatorial studies. Conversely, data from combinatorial studies may also be fed back into computer modeling studies to help further refine the steric restrictors.

It should be understood that although microbead solid phase peptide synthesis methods have been used as examples in this discussion, many other synthetic peptide synthesis methods may also be used.

Labeling Techniques:

The labeling methods used for enzymatic assays employing steric restrictor modified peptide substrates will vary depending upon the details of the particular enzymes and assays in question. Kinases and peptide substrates for kinases, will often be labeled with radioactive phosphorus ($P^{32}$), and monitored by radioactivity detection methods. For many protease assays of endopeptidases that use two different steric restrictors, one located on the "N" terminal end of the substrate peptide, and the other located on the "C" terminal end of the substrate peptide; dual label methods may be appropriate. Here the combination labels of the prior art, such as paired fluorescence, fluorescence-quencher labels on opposite sides of a protease peptides scissile bond, are useful.

For other endopeptidase assays, and/or exopeptidase assays where only a single steric restrictor moiety may be bound to only one side of the substrate peptide, labels of the prior art are less useful. Exopeptidases cleave the outmost amino or carboxyl terminals of peptides, and the act of placing a quencher moiety on the terminal end may have the unwanted side effect of protecting the peptide from attack by the very protease that an experimenter may wish to monitor.

In order to apply steric restrictor concepts to some endopeptidases and most exopeptidases, an ideal label will both enable exopeptidase activity of a peptide substrate be detected, and also allow a library of various steric restrictor moieties to be constructed in order to enhance the specificity of the exopeptidase reaction.

The N or C terminal peptide labels of the prior art do not lend themselves to incorporation into steric restrictor libraries. Ideally, an exopeptidase label suitable for incorporation into a steric restrictor moiety should contain two functional groups in addition to the label moiety itself. One functional group should be the substrate peptide, and exopeptidase cleavage of this peptide should produce a detectable signal. A second functional group should be the steric restrictor group. Often it is particularly advantageous if this steric restrictor group be a peptide group that can be designed in a variety of alternate sequences and conformations, and that is resistant to protease attack. An ideal exopeptidase label would be incorporated in the joint region between the exopeptidase substrate peptide, and the steric restrictor peptide. Thus such an ideal exopeptidase label would be divalent, with an amino or carboxyl group suitable for binding to a substrate peptide on one side, and an amino or carboxyl group of opposite polarity (type) suitable for binding to a steric restrictor peptide on the other side. This polarity enables the formation of a longer [substrate peptide]-[label linker]-[steric restrictor peptide] entity.

Labels of the prior art were either monovalent (e.g. only one peptide group), or ineffectively divalent (e.g. two identical peptide groups, both peptides presenting the same terminus to the outside environment, or one peptide binding group, and one solid phase support binding group).

Here, methods are disclosed to convert label moieties, where each label moiety has a divalent reaction site of the same polarity, such as Rhodamine 110, into alternative label moieties, better suited for steric restrictor applications by reaction with cross linker molecules. These techniques can create label moieties with two peptide-binding regions in the correct opposite polarity.

As an example, to convert a Rhodamine 110 label moiety, which presents two N terminals of two identical peptide groups to the outside environment, to an alternate Rhodamine 110 label moiety presenting two different peptide groups to the outside environment, one peptide group presenting an N terminal end, and the other peptide group presenting a C terminal end, the following procedure may be employed.

1: Prepare Rhodamine 110 (amino acid)$_2$-CBZ moieties following the methods of Mangel, et. al. U.S. Pat. No. 4,557,862. If CBZ is not desired as a blocking group, other blocking groups may alternatively be used. This first amino acid will be designated aa1. Typically, aa1 will correspond to the C terminal end of the substrate peptide for the particular protease under investigation, so that cleavage of aa1 from the Rhodamine 110 moiety produces a fluorescent signal.

2: Subject the purified Rhodamine 110 (amino acid)$_2$-CBZ to limited proteolytic digestion using an exopeptidase appropriate to the amino acid in question. This will produce a mixture of free Rhodamine 110, Rhodamine 110 (amino acid)$_2$-CBZ, and Rhodamine 110 (amino acid)$_1$-CBZ. Quench the reaction adding an enzyme inhibitor, or denaturing the enzyme by adding appropriate denaturing chemicals to the solution.

3: Purify Rhodamine 110 (amino acid)$_1$-CBZ by chromatographic or other means

4: Separately, mix an N terminal crosslinking agent, such as DMS imidoester (dimethyl suberimidate, Pierce Inc., Rockford, Ill.) with a second amino acid (aa2). Typically aa2 will serve as a part of the steric restrictor moiety, and thus may be selected to be resistant to further proteolytic attack. Amino acid (aa2) should be in excess in this reaction so as to produce a population consisting of DMS(aa2)$_2$ molecules.

5: Combine Rhodamine 110 (amino acid)$_1$-CBZ with an excess of DMS(aa2)$_2$, and react to form the composite molecule:

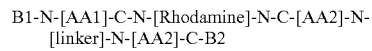

Where B1 and B2 are the appropriate N terminal and C terminal blocking groups.

6: Build up the steric restrictor peptide using standard solid phase synthesis techniques. Keep this bound to the solid phase support.

7: Build up all elements of the substrate peptide, with the exception of aa1, using solid or liquid phase synthesis as appropriate.

8: Couple the composite molecule B1-N-[AA1]-C-N-[Rhodamine]-N-C-[AA2]-N-[linker]-N-[AA2]-C-B2 to the steric restrictor peptide using standard solid phase synthesis techniques, producing:

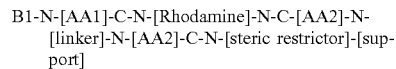

9: Couple the substrate peptide to the composite linker molecule-steric restrictor-support from (8) using standard solid phase synthesis techniques.

10: If desired, cleave (9) from the solid phase support using standard solid phase peptide synthesis cleavage techniques, producing:

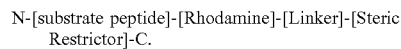

Figure 4:
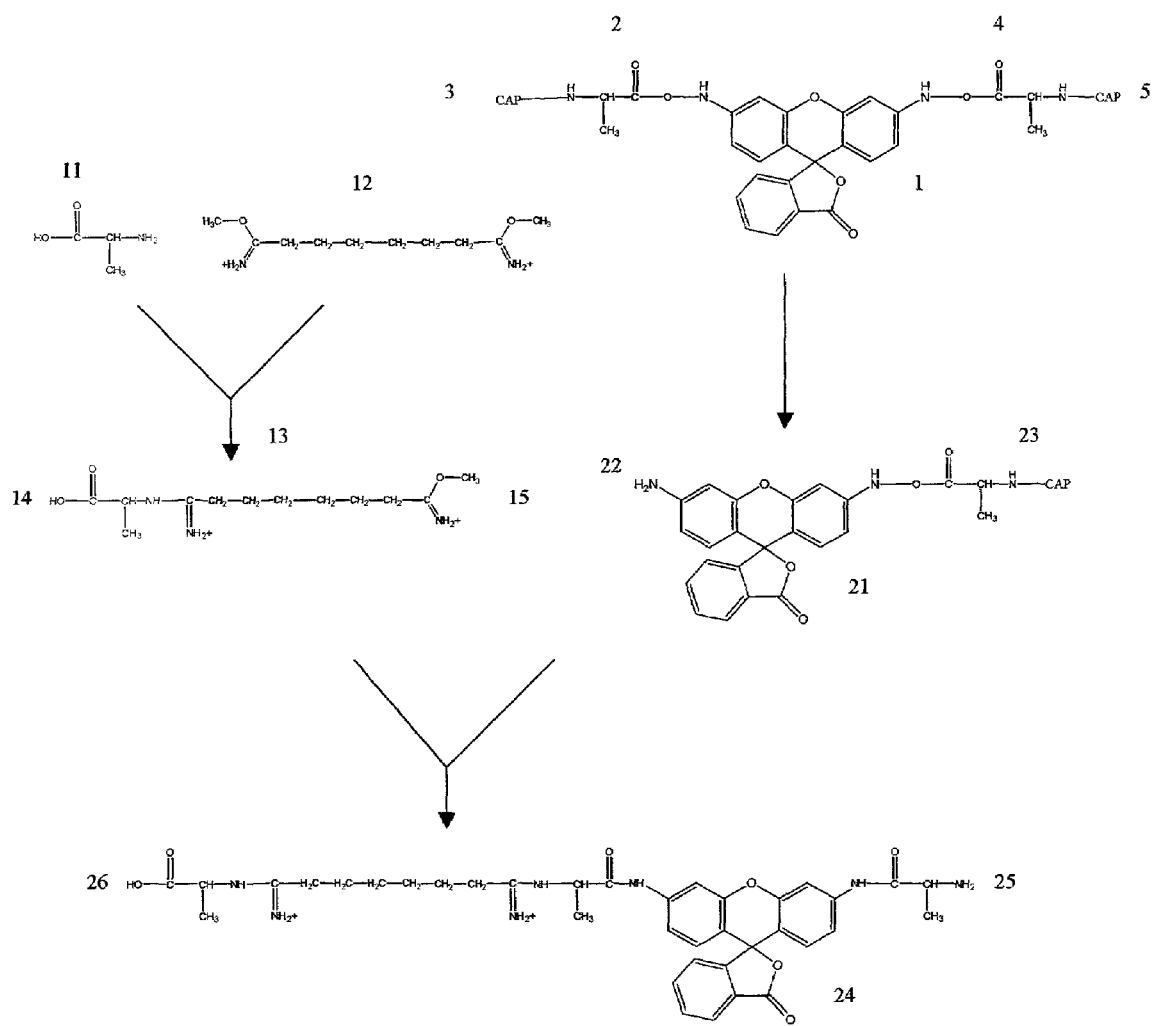
FIG. 4 shows a Rhodamine 110 molecule modified for steric restrictor use

FIG. 4 shows more of the details of this reaction scheme. Here a divalent Rhodamine 110 molecule (1), with its fluorescence quenched by linkage to the carboxyl terminal ends of two identical amino acids (2, 4) (here alanine is illustrated) with N-terminal caps (3, 5) is used as the starting point of the reaction. This Rhodamine molecule is subjected to partial proteolytic digestion, and the reaction products corresponding to Rhodamine-110 (21) coupled to a single amino acid (23), and a free amino group (22) are purified, typically by chromatographic means.

In a parallel path, a second amino acid (11) (for simplicity, alanine is again illustrated) is cross-linked at its amino terminal end with a divalent DMS crosslinker (13) in a reaction with excess amino acid, forming a monovalent DMS-amino acid molecule (13), with the carboxyl terminus of the amino acid at one end (14), and the reactive amino terminal end of the DMS crosslinker at the other end (15). This is then purified from the excess amino acid and unreacted DMS.

The DMS-amino acid molecule (13) and the monovalent Rhodamine-110 molecule are then coupled following the methods of Mangel et. al. This forms a composite Rhodamine-110 molecule (24) containing the amino terminal of one amino acid at one end (25), and the carboxyl terminal of a second amino acid at the opposite end (26). Note that for simplicity sake, the drawing of the amino terminal blocking "CAP" group has been omitted from the drawing.

The composite Rhodamine 110 structure may then be used in standard peptide synthesis reactions, where the carboxyl terminal will typically be attached to a steric restrictor group, and the amino terminal will typically be attached to the cleaveable moiety of a protease substrate peptide, so that proteolytic cleavage of the amino acid residue (25) will restore Rhodamine fluorescence.

This molecule may be rebound to solid phase supports (beads, pins, microplate wells, microarrays, etc.), or alternatively used to convey additional specificity to liquid phase protease assays.

It should be evident that a number of variations on the synthetic strategy disclosed herein will also work. For example, the Rhodamine label can be first synthesized with two duplicate copies of either the entire substrate peptide or the entire steric restrictor molecule, and one cleaved off. Alternatively, the linker molecule may be directly coupled to the steric restrictor molecule.

Microarray Construction Techniques

Microarray solid support: Depending upon the application, the enzymatic substrate microarray will be constructed on a solid surface that may be either flat or non-flat, and may be either porous or non-porous. If the synthetic peptides are non-lipid-membrane associated and are arrayed by pin-spotting techniques, generally flat non-porous substrates are preferred. If the synthetic peptide substrates are lipid-membrane associated, it may be preferable to use solid supports containing multiple micro-ridges, wells, or divisions, following the techniques of Boxer (WIPO PCT publication WO9823948A1). The peptides should be bound to the surface, either covalently, or noncovalently, as to preserve their dimensional location upon sample application, and possible subsequent incubation and washing steps. Exemplary surfaces include glass, plastic, silicon or the like. Generally non-porous substrates are preferable, but porous substrates may be used provided that the porous surface accommodates the precise dimensional localization of the applied peptide array elements.

Figure 5:
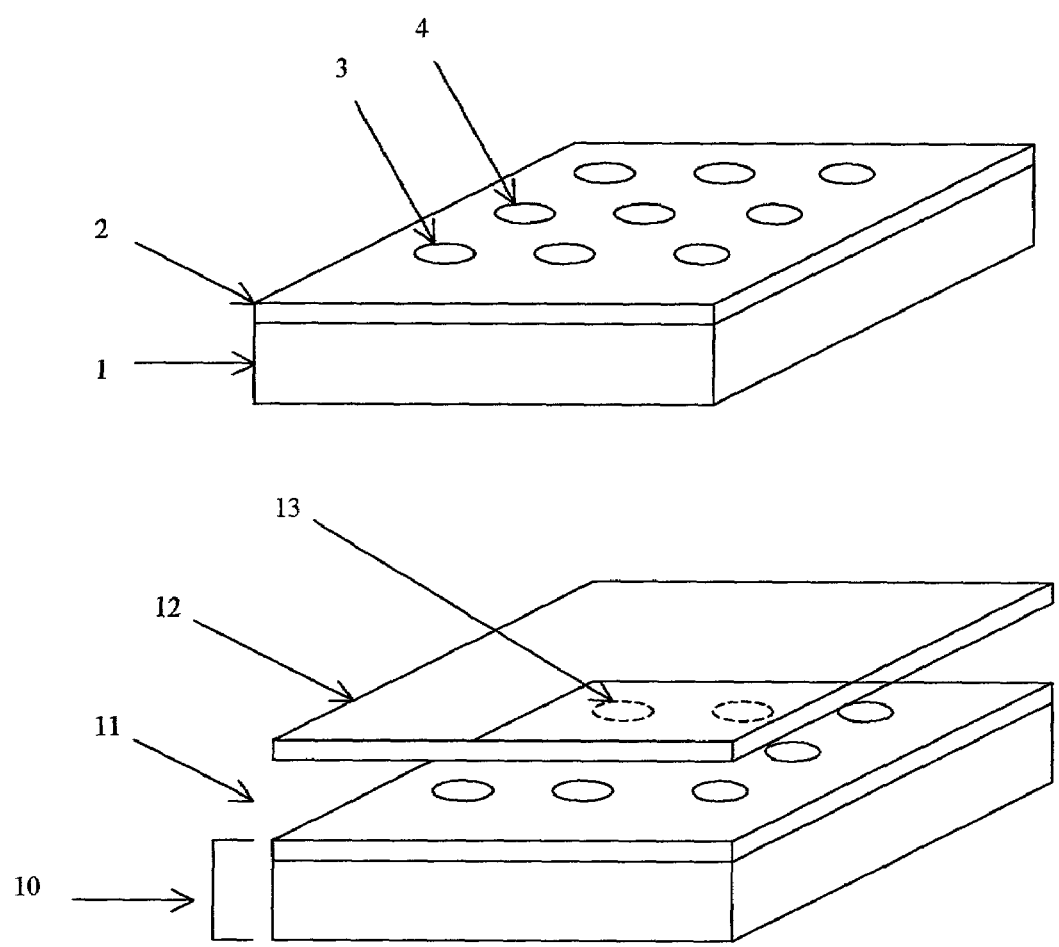
FIG. 5 shows an exemplary overview of an enzyme substrate microarray.

FIG. 5 shows an exemplary enzyme substrate microarray constructed according to the teachings herein. Substrate (1) may be treated or coated with an optional coupling layer (2) to enhance peptide binding and/or to facilitate subsequent detection of peptide cleavage. Here, any of the peptide binding methods, previously discussed, may be used. An array of small, closely spaced, peptide zones (3), (4), typically each zone having a different peptide sequence, is spotted or synthesized on the substrate. This will typically be followed by a washing step in which any unbound peptides are washed away from the surface of the microarray. Depending upon the application, the microarray may usually (but now always) be stored in a dry form until use.

For protease substrate microarrays, the peptides on the microarray will further contain detection moieties (fluorescent tags, fluorescent quenchers, etc.) to generate a detectable signal corresponding to the level of proteolytic cleavage of the particular peptide zone in question. The peptides are bound to the substrate (either covalently or non-covalently) to the extent sufficient to prevent diffusion of the bound peptides upon application of liquid sample, and subsequent digestion and processing steps.

In use, the completed microarray (10) is exposed to a liquid sample (11), which may contain proteases, suspected proteases, a mix of unknown proteases, a mix of proteases and protease response modifying agents, etc. The sample will typically be covered with an optional cover (12) to help distribute the sample evenly over the array, and to prevent evaporation. Typically the cover will be of a transparent flat material, such as a glass or plastic cover slip, to enable observation of the peptide zones (13) during the course of the digestion reaction. During the protease digestion reaction, peptides with differential sequences will typically be digested to a differential amount. The detectable signal generated by the detection moieties attached to each peptide region will be interrogated, typically at multiple time points during the digestion reaction. This conveys information as to the specificity or specificities and relative proteolytic activity of the unknown sample. Optionally, at the end of the reaction, a non-specific protease or other non-specific labeled moiety reacting agent may be added to the microarray to serve as a positive or negative control.

If a kinase substrate microarray is being used, the reaction buffer may contain compounds with radioactive phosphorous ($P^{32}$), which may be incorporated into the kinase substrate peptides during the course of the reaction.

Peptide binding considerations: Often, microarrays will have chemical side groups that preferentially bind only the "N" or "C" terminals of the peptides. Although this may suffice for many purposes, in some situations it may be preferable to present all sides of the synthetic substrate to the applied enzymes. Here, the microarray should accommodate peptides bound at either the N or C terminus.

Figure 6:
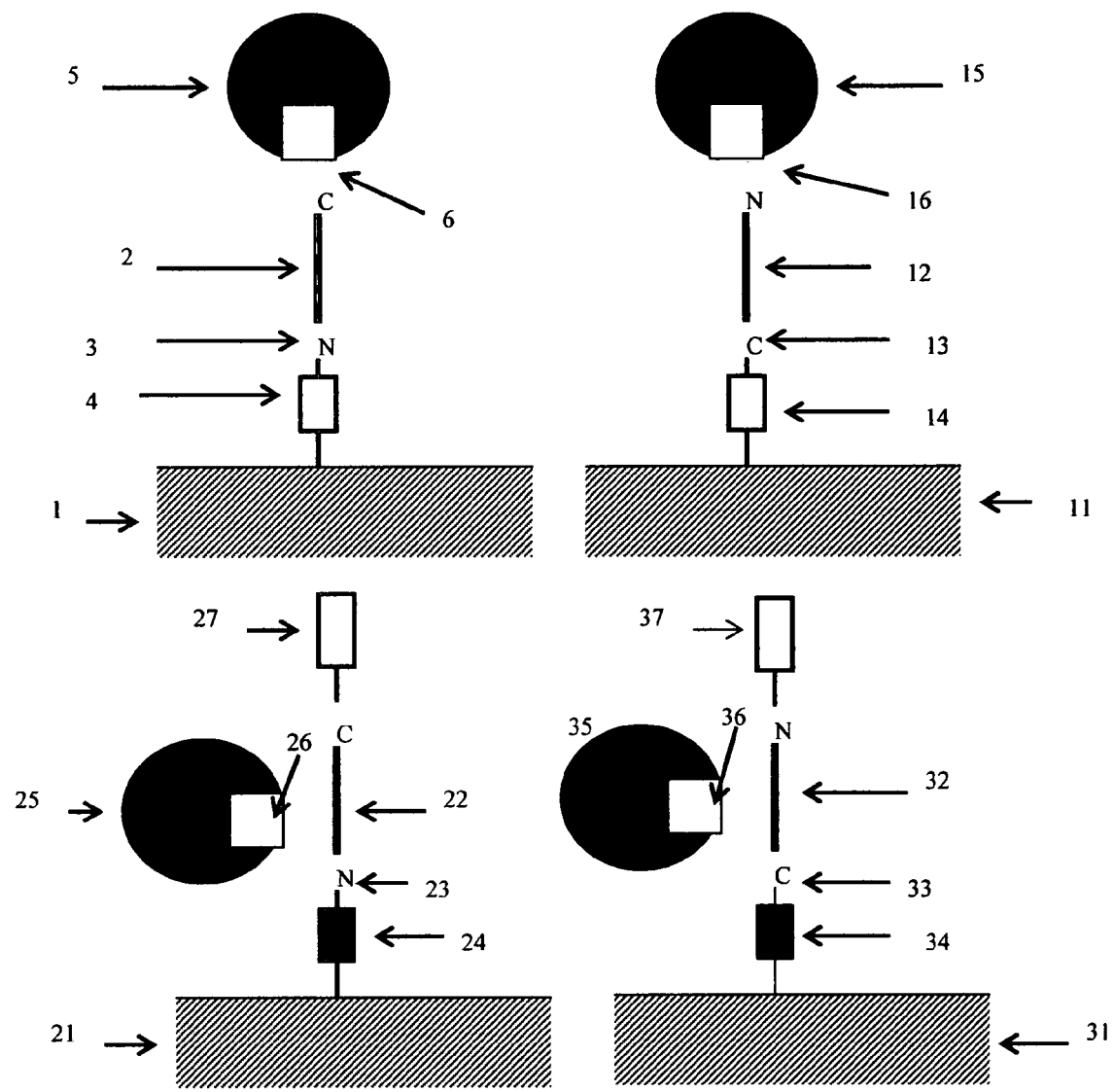
FIG. 6 shows various ways in which peptides may be attached to the microarray substrate

Examples of some of the alternative peptide binding and labeling methods that may be used with the microarray of this invention are shown in FIG. 6. Proteases analyzed by the microarray may include exopeptidases that degrade peptides from either the "N" amino terminal end (aminopeptidases), the "C" or carboxyl terminal end (carboxypeptidases), or alternatively may be endopeptidases and cleave the peptide somewhere in the middle. This aspect may be used to "tune" the protease specificity of the microarray. For microarrays designed for characterization of complex protease mixtures (e.g. from tissue samples, and the like), it may be preferable to design the array so that a given peptide exposes its "N" terminus in one zone of the array, and again exposes its "C" terminus in a different zone of the array. Alternatively, if it is desirable to interrogate only one general class of proteases (e.g. only aminopeptidases, only carboxypeptidases, or only endopeptidases), all the peptides may be bound in a single configuration.

Peptide labeling considerations: A variety of methods may be used to label the peptides employed in the array. These methods include those previously discussed, as well as other fluorescence, fluorescence quenching, fluorescence transfer, electrochemiluminescence, luminescence, radioactive, enzymatic detection, and antibody detection means.

In order to produce a genuinely useful protease substrate microarray, a number of labeling and signal detection issues must be considered. Due to variations in peptide application, binding and retention efficiency, there typically will be substantial differences in the number of peptide molecules bound per array location. Often these will vary by more than a factor of two between neighboring array locations. A protease (or other enzymatic) detection scheme that relies on monitoring the disappearance of a direct peptide label, such as a direct fluorescent label, will be hampered by the significant variation in peptide amounts per array location. Thus these label disappearance methods are less favored. Alternative label methods, which generate a signal only upon proteolytic cleavage (or other enzymatic action upon) of the substrate peptide are preferred, since the initial onset of signal (when most of the peptides remain uncleaved) will be relatively unaffected by variations in the absolute number of peptides bound, and thus better reflect the true levels of enzymatic activity.

The extent of proteolysis or other enzymatic activity can be monitored either continuously or discontinuously during the course of the enzymatic reaction, typically by optical detection methods. Alternatively, the reaction may be terminated, and the microarray may then be "developed" by processing with subsequent agents (enzyme labels, antibody labels, etc.) in order to assess the relative amounts of reacted substrate peptides. Typically a kinase substrate assay will be assessed this way. For example, a photographic emulsion will be brought into contact with the microarray, and the radioactivity of the various substrate zones assessed, following the methods of MacBeath and Schreiber *Science* 2000, 289, 1760-1763.

In a preferred embodiment, the labeling system will generate a positive signal in response to the enzymatic reaction of any given peptide substrate in question. This will facilitate distinguishing partially reacted zones from non-reacted zones.

The steric restrictor and labeling scheme used may differ according to the desired microarray specificity. For exopeptidases that cleave from either the "N" or "C" terminal end, it may be advantageous to use steric restrictors containing a label with a detectable signal that is quenched when a peptide is attached to the moiety. For endopeptidases, the same scheme may be used, or alternatively it may be advantageous to use alternative labeling systems, such as dual fluorophorelfluorescence quencher labels, wavelength shifter/fluorophore labels, dual luminescence, chemoluminescence, electrochemoluminescence label/quencher combinations, etc. Here, proteolytic cleavage frees the steric restrictor containing the quencher moiety from the substrate bound steric restrictor containing the light-emitting moiety, enabling the extent of proteolysis to be assessed.

FIG. 6 shows examples of some of the peptide binding schemes and labels that may be used in the microarray of this invention. (For simplicity, details of the steric-restrictor/enzyme interactions, previously drawn in FIGS. 1-3, are not shown in FIG. 6). Here the microarray is formed on substrate (1, 11, 21, 31). Peptides (2, 12, 22, 23) may be bound to the substrate side steric restrictor by their "N" terminal ends (3, 24) or "C" terminal ends (14, 34). In an alternative embodiment (not shown), both ends may be bound, forming a loop. Various labeling schemes may be employed to detect proteolytic cleavage. In one embodiment, the "N" terminus or "N" terminal side group of the peptide may be linked to a steric restrictor and label moiety (4) that produces a detectable signal upon peptide cleavage and that remains bound to the microarray substrate. In an alternative embodiment, the "C" terminus or "C" terminal side group of the peptide may be linked to a steric restrictor and label moiety (14) that produces a detectable signal upon peptide cleavage by active site (6, 16) of protease (5, 15). Alternatively (not shown), the peptides may be labeled with a detectable moiety attached to the portion of the peptide that will be cleaved by the protease, and proteolytic digestion assessed by monitoring the loss of this steric restrictor bound detectable moiety.

Alternatively, protease activity may be monitored by cleavage of a detectable moiety/detectable moiety quencher system. Here peptides (22, 32) may be bound to substrate (21, 31), and also bound to steric restrictor containing a detectable moiety (24, 34) that will remain associated with the microarray surface (21, 31) after proteolytic cleavage. As before, the peptides can be bound by their "N" terminal end (23), their "C" terminal ends (33), or both ends (not shown). Attached to the part of the peptide that is liberated from the substrate by proteolytic cleavage by active site (26, 36) of protease (25, 35) is the steric restrictor containing the complementary quencher moiety to the detectable moiety. Upon proteolytic cleavage, the quencher moiety diffuses away from the detectable moiety, producing a detectable signal.

Lipid-Membrane-bound protein substrate targets: Occasionally, enzymatic substrate targets of interest may be lipid-membrane-bound protein substrates, with certain unique steric constraints imposed by the protein-lipid interactions. In the event that synthetic steric restrictor moieties do not suffice to reproduce the specificity of the naive lipoprotein complex, use of microarrays containing artificial lipid membranes may be employed. Here, the methods of Boxer (WIPO PCT publication WO9823948A1) may be used.

Array spotting considerations: Generally, proteins will be spotted onto solid supports using microfuidic and pin printing techniques as described by Rose, "*Microfluidic technologies and instrumentation for printing DNA microarrays*", Chapter 2, pp 19-38, or Mace et. al., "*Novel microarray printing and detection technologies,* Chapter 3 pp 39-64, both in, *Microarray Biochip Technology* (2000), Schena Editor, BioTechniques Books, Natick, Mass., the contents of which are incorporated herein by reference.

Reaction optimization considerations: In order to maximize the specificity of the assay, enzymes may be applied to the microarray in a variety of concentrations, reaction chemistries (varying pH, salt content, cofactor content, etc.), and temperatures.

Microarray reading considerations: The microarrays may be read by a variety of methods. Because important information is contained in the differential kinetics of cleavage between the different peptides in the array, reading methods that monitor multiple array elements as a function of time are favored.

One simple method is video microscopy, in which large sections of the array, or the entire array, are imaged by fluorescent or luminescent video microscopy. Alternatively, scanning microscopy, in which an optical read head or sensor is scanned across the array, may also be used. Ideally, the video pixel elements corresponding to each array element are digitized and the relative rates of signal appearance normalized to various "control" reference array elements. A number of different types of reference array elements may be chosen. One type of reference element may be composed of peptides with one or more binding sites for the less specific enzymes. This type of reference element will tend to react with the least specificity and the highest speed, and serves as a good marker to indicate the background "noise" level of the assay. A second type of reference element may be composed of peptides with sequence or amino acid composition known to be highly refractory to enzymatic modification. Such peptides may be constructed of unnatural (synthetic) amino acids of the wrong chirality, or with side groups that do not naturally occur in nature. This reference element will generally serve as a good marker to indicate if improper processing of the microarray has occurred. Other reference elements may be included as appropriate to the specifics of each microarray.

Figure 7:
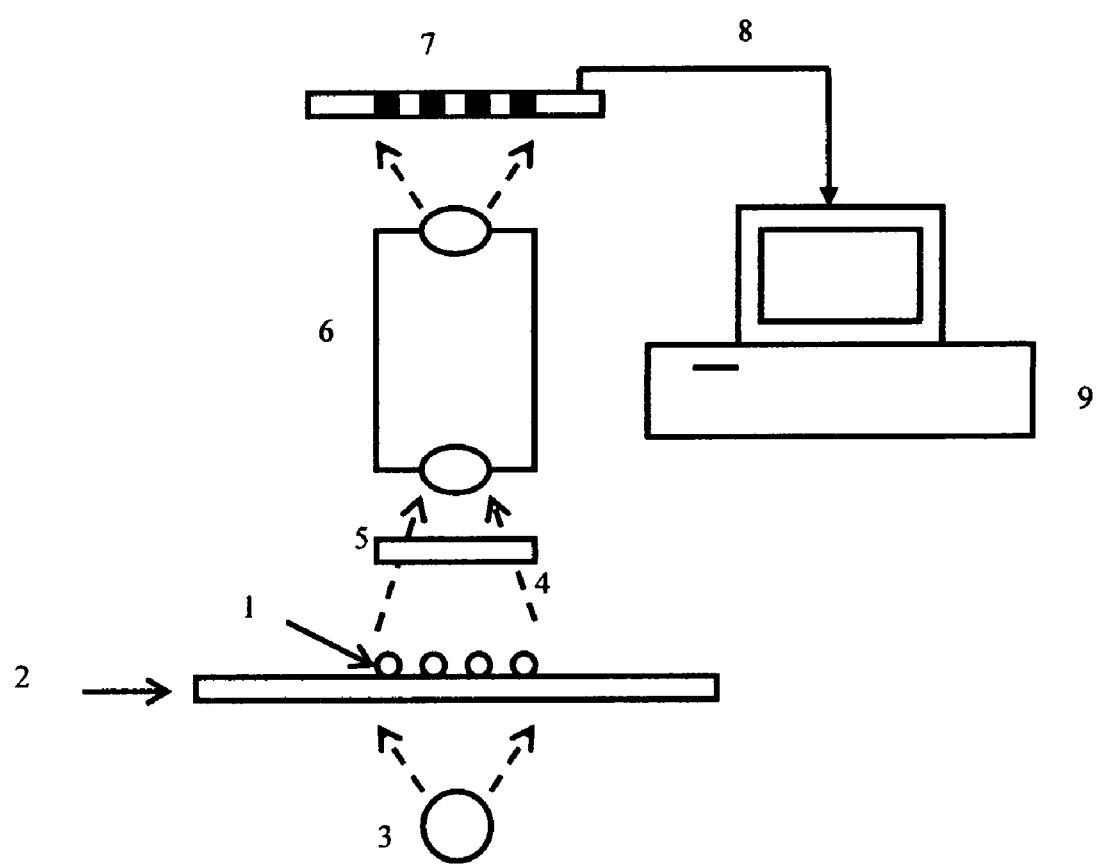
FIG. 7 shows a reader for a protease substrate microarray

An example microarray detector system with a single read-head is shown in FIG. 7. Here labeled peptide zones (1) on microarray substrate (2) may be activated or energized by light signal, chemical solution, or electrical signal (3). In this specific example, a fluorescent light source (3) illuminates the microarray (from either a light conducting top cover (not shown), or through a light conducting substrate (2). Signal (4) from the labeled peptides travels through optional optical filter (5), which may be used when fluorescent labels are employed. Signal (4) is detected by reader (6), which will typically be either a stationary or moveable microscopy optical pickup. The output from the reader will typically be converted to electronic form and optionally digitized by detector (7), which may be a photodetector or video detector. The output from detector (7) is then typically fed to a computer, where the signal originating from each peptide array location may be correlated with the peptides sequence, using the peptide location records that were created when the microarray was originally produced.

For some applications, it may be desirable to employ microarray detectors with multiple read heads, so that multiple protease digestion or other enzymatic reactions on multiple arrays may be performed simultaneously. Such multiple read-head systems can be useful for experiments where simultaneous analysis of a biological sample at multiple dilutions, in the presence or absence of additional enzymatic cocktails, or in the presence or absence of agents that modify enzymatic activity; is desired. Multiple read-head systems are also advantageous for higher-throughput drug screening applications.

Although optical techniques lend themselves well to protease microarrays, electronic techniques may also be used. For example, peptides may be spotted on the surface of an electrode grid, and protease activity monitored by electronic means. Alternatively, radioactivity-monitoring methods may also be used.

Applications

Protease specificity discovery kits: Proteases often recognize short sequences of amino acids, typically 2-4 amino acids in length. Using microarray techniques and conventional microspotting methods, microarrays with a spot density in excess of 40,000 to 160,000 spots per slide can be constructed (Genpack Array™ 21, robotic microarrayer system, Genpack corporation, Stony Brook, N.Y.).

For such larger arrays, it may be preferable to construct "generic" classes of steric restrictor moieties, appropriate to multiple members of a particular enzymatic family or subfamily, rather than to attempt to define a unique steric constrictor for each of the thousands of different peptide combinations.

Figure 8:
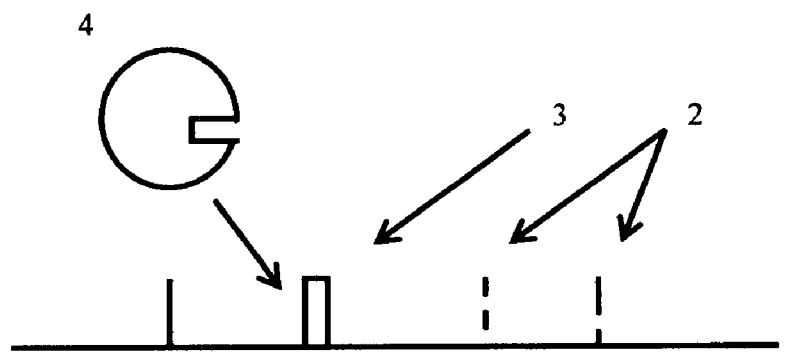
FIG. 8 shows an application for the microarray for protease characterization
Figure 8:
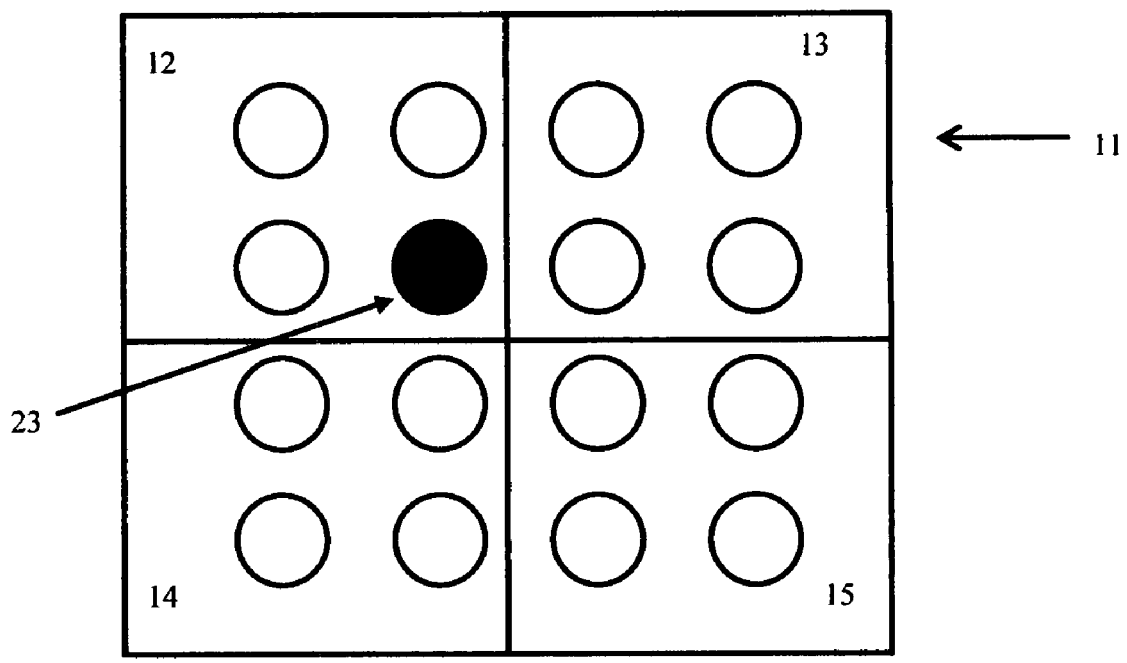

One of the simplest applications of the microarray is shown in FIG. 8. In this simple application, the microarray is used to map out the peptide sequence specificity of a single purified protease. To do this, the surface of the microarray (1) is given an array (2,3) of all possible or all likely peptide sequence combinations, bound to various sets of generic steric restrictors. The purified enzyme sample (4) is then allowed to react to the array, and the results monitored. Here the enzyme is assumed to react with peptide sequence (3) but not the other peptide sequences (2).

The results of the protease digestion are shown in a schematic top view of the microarray (11). In this example, the array is divided into quadrants (12, 13, 14, 15), each quadrant presenting the same array of peptide substrates in the context of a different, quadrant specific, generic steric restrictor. In one array location (23) the peptides of sequence (3) has reacted with the protease, suggesting that the protease has specificity for this particular sequence in the context of the quadrant 12 steric restrictors, but not in the context of the quadrant 13, 14, or 15 steric restrictors. By contrast, nearby substrate peptide candidates with different sequences are not reacted.

Here, the power of the protease substrate microarray method starts to become evident. Using conventional spotting equipment developed to produce nucleic acid microarrays; it is possible to spot up to 160,000 samples in the space of a single microscope slide. There are 20 amino acids in biological proteins. Using these techniques, a researcher could rapidly, and with only a few microliters of sample, and in a few minutes, map out the full extent of the specificity of the enzyme to all combinations of tripeptides ($20^3$=8000 samples), constrained by 20 different types of steric restrictors. Conversely, one substrate peptide could be mapped out in the context of 160,000 different steric restrictors, 20 substrate peptides could be mapped out in the context of 8,000 different steric restrictors, and so on.

The same techniques can be applied to discover entirely new types of proteases (and other enzymes). For example, it is known that proteolytic cleavage of standard coagulation factors and tissue matrix proteins can produce short peptides that modulate (either stimulate, or inhibit) angiogenesis. However it is unlikely that all such factors have been found. An angiogenesis factor discovery kit could be produced by producing an array based upon short peptides produced from the standard coagulation factors and tissue matrix proteins, such as collagen. Such peptides might simply be produced by walking from one end of the protein sequence (a, b, c, d, e, f, g, h, . . . ) to the other end, and producing a peptide library that corresponds to many possible clevage sequences (e.g. [a, b, c, d], [b, c, d, e], [c, d, e, f] etc), and combined with a library of "generic" steric restrictor moieties. Cell extracts from angiogenic and non-angiogenic sources could be applied to such arrays. The presence of a new pattern of proteolytic activity in samples with unusually high or low levels of angiogenesis would suggest the possibility that a new type of protease was producing a new type of angiogenesis response modifying peptide.

Medical Research

Protease substrate microarrays can be useful in many areas of medical research. As an example, protease cascades consisting of multiple interacting proteases and protease substrates regulate many biological processes. Well-known examples include the various proteolytic cascades used to regulate apoptosis (cell death). Apoptosis plays an important role in many important biological events, including embriogenesis, immune responses, autoimmune diseases, stroke, myocardial infarction, rheumatoid arthritis, and cancer. Apoptosis is regulated by a number of different proteases, including the caspase family of proteases. This protease family is regulated by a network of stimulators and inhibitors, which contains over 50 different components. Here micro-methods capable of comprehensibly analyzing the spectrum of proteolytic activity, using only small quantities of tissue, are quite useful.

Medical Diagnostics

Many proteases, and other enzymes, have extremely short half-lives, often on the order of a few minutes. Here, enzyme substrate microarray techniques have a significant advantage over conventional techniques, because they make it possible to assay large numbers of potential enzymatic substrates simultaneously and immediately after receipt of a biological sample.

Some of the areas where protease substrate microarray techniques may be useful include angiogenesis assays for cancer and other vascular proliferative disorders, coagulation abnormality assays, arthritis status assays, and many other disease processes.

To illustrate this point, the utility of protease substrate microarrays for angiogenesis assays will be examined in detail.

As previously discussed, angiogenesis is regulated by a fairly large number of proteases and proteolytic fragments. Proteases are involved in both the positive and negative control of angiogenesis. Upon receiving an angiogenic signal, endothelial cells produce proteases, such as the matrix metalloproteases, that degrade extracellular matrix proteins. The endothelial cells then typically proliferate, migrate into the degraded tissue, and form new blood vessels. Higher levels of some of these proteases thus serve as a positive stimulator for angiogenesis. However other proteases act to produce angiogenic inhibitors.

Tumor growth is controlled by a balance between positive and negative angiogenesis signals. If positive signals predominate, the tumor will become vascularized and grow. If negative signals predominate, the tumor will not become vascularized, and remain dormant. Tumors generate both positive and negative angiogenic factors, and an understanding of which specific factors are being generated is highly important for cancer therapy.

As an example, often a large and rapidly growing primary tumor may be surrounded by numerous small, no-vascularized, satellite tumors, often nearly microscopic, that are apparently dormant. Upon surgical removal of the large primary tumor, however, the "dormant" satellite tumors will quickly become vascularized and start to grow rapidly. This is because the large tumor was secreting angiogenesis stimulators with a short lifetime, and angiogenesis inhibitors with a longer lifetime. In the large tumor itself, the effect of the short lifetime stimulators predominated, causing local growth. Further from the tumor, the effect of the longer lifetime inhibitors predominated, resulting in a suppression of the satellite metastatic tumors. In this situation, removal of the primary tumor can have the undesired effect of removing the inhibition source for the smaller tumors, resulting in an unfavorable outcome.

Ideally, what is needed is a test for a tumor's angiogenic status that can be rapidly performed using a tissue biopsy or surgical specimen, and that can give an accurate overview of the various angiogenic stimulators and inhibitors produced by a particular tumor. This test may be used to assess the relative malignancy of a particular tumor. Tumors with a low level of angiogenesis stimulators, or a high level of angiogenesis inhibitors, would be expected to be less malignant. Conversely, tumors with a high level of angiogenesis stimulators or low level of angiogenesis inhibitors would be expected to be more malignant. Depending upon the outcome of the test, different surgical procedures or alternative anti-angiogenic drugs may be given. With more information, better medical decisions can be made, resulting in improved outcomes.

At present, there is no good way to assess the spectrum of various protease activities in a tissue biopsy except by immunochemical staining methods. Here a tissue sample is obtained, chemically fixed with a preservative, and sectioned into thin slices for microscopic examination. These tissue sections can then be stained with labeled antibodies against one or more suspected proteases, and examined under a microscope. Because the antibody detects antigenic activity, rather than proteolytic activity, it is difficult to ascertain if a positive immunochemical reaction is due to binding to an activated form of the protease, or binding to an inhibited or inactive form of the protease.

The crude protease detection methods of prior art are also problematic, due to the previously mentioned short half-life of a number of angiogenesis proteases and protease inhibitors. Other problems include the small amounts of material produced by common needle biopsy techniques, and the complex mix of both proteases and protease inhibitors. Traditional biochemical protease assays, which often rely upon a number of slow intermediate steps involving isolation and partial purification of larger sample sizes, will often lead to an incorrect assessment of the proteolytic status of a tissue sample, and thus an incorrect angiogenic status. In particular, it should be evident that it will be difficult to characterize complex patterns of protease activity by use of immunochemical staining techniques.

Here, microarrays of the present invention, which can rapidly scan the entire spectrum of possible proteases, protease inhibitors, and protease stimulators, using fresh, small sized specimens from a tissue biopsy, are highly useful.

Here, an example of a protease substrate microarray designed to assess the angiogenic status of tissue samples is given.

Protease substrate microarray useful for assessing the angiogenic status of a tissue sample:

A list of some of the protease/proteolytic fragments relevant to angiogenesis is shown in Table 1, which is taken from data compiled by Pepper, "*Role of the Matrix Metalloproteinase and Plasminogen Activator-Plasmin Systems in Angiogenesis*" *Artherioscler, Thromb. Vasc. Biol.* July 2001, 1104-1117; Zhand and Bicknell *"Therapeutic Inhibition of Angiogenesis"*, *Angiogenesis Protocols*, Murray (2000), Humana Press, Totowa, N.J., Browder et. al. *The Hemostatic System as a Regulator of Antiogenesis* (2000). *J. Bio. Chem* 275 (3), 1521-1524, and Zucker et. al., "*Critical appraisal of the use of matrix metalloproteinase inhibitors in cancer treatment*", *Oncogene* (2000) 19: 6642-6650).

TABLE 1

Partial list of the proteases, protease substrates, and protease factors known to be involved in angiogenesis.

| Protease | Protease substrate | Inhibitors | Proteolytic fragment |
| --- | --- | --- | --- |
|  | TGF-β activation |  | Cytokine (S) |
|  | Matrix bFGF release |  | Cytokine (S) |
|  | Matrix VEGF release |  | Cytokine (S) |
|  | Membrane TNF-α release | TIMP-3 | Cytokine |
|  | MCP-3 |  | Chemokine antagonist |
| MMP-1 | pro-MMP-2, | TIMP-2,3, Endostatin, PEX | Active MMP-2, PEX |
| MMP-2 | Plasminogen | TIMP-2,4, thrombospondin 1,2 | Angiostatin (I) |
| MMP-3, | Plasminogen |  | Angiostatin (I) |
| MMP-9 | Plasminogen | TIMP-1 | Angiostatin (I) |
| MMP-7 | Plasminogen |  | Angiostatin (I) |
| MMP-12 | Plasminogen |  | Angiostatin (I) |
| MMP-12 | u-PA receptor (u-PAR) |  | D1 domain (I) |

TABLE 1-continued

Partial list of the proteases, protease substrates, and protease factors known to be involved in angiogenesis.

| Protease | Protease substrate | Inhibitors | Proteolytic fragment |
|---|---|---|---|
| tPA | Plasminogen | PAI-1 | Plasmin & factors |
| uPA | Plasminogen | | Plasmin & factors |
| MMP-2 | Collagen IV | | MMP-2 generated fragments (I) |
| | Collagen IV | | Arresten (α1 chain) (I) |
| MMP-9 | Collagen IV | | Canstatin (α2 chain) (I) |
| | Collagen IV | | Tumstatin (α3 chain) (I) |
| | Collagen XV | | Restin (I) |
| Cathepsin L | Collagen XVIII | | Endostatin (I) |
| Cathepsins | Collagen XVIII | | Endostatin (I) |
| Elastase | Collagen XVIII | | Endostatin (I) |
| MMPs | Collagen XVIII | | Endostatin (I) |
| | Thrombospondin | | (I) |
| | Hyaluronan | | (S) |
| | SPARC | | KGHK fragments (I, S) |
| | Prolactin | | 16K PRL fragment (I) |
| | Platelet factor 4 | | N-terminal end (I) |
| | MMP-2 | | PEX (I) |
| neutrophil elastase, thrombin | Antithrombin III | | anti-angiogenic AT-III (I) |
| | Calreticulin | | Vasostatin (I) |
| Kallikrein | HMWKinnogen domain 5 | | Kininostatin (I) |
| Thrombin | Endothelial cell thrombin receptor | Prothrombin fragments 1 and 2 | |
| MT-MMP-1 | Fibrin | | |
| MMP-9 | Fibrin | | |
| Cathepsin-B | TIMP-1, TIMP-2 | | degradation of inhibitors |
| | EGF | | Peptide fragment aa's 33-42 (M) |
| | Fibrinonectin | | 29 kD fragment (P) |
| Thrombin | Osteopontin | | RGD fragment ? |

An angiogenesis status microarray may be created by constructing an array of synthetic protease substrates from the known angiogenesis protease substrate proteins. In the case of the above list, many such substrate peptides have previously been identified in the literature. For those that have not, the methods of Harris et. al., *"Rapid and general profiling of protease specificity by using combinatorial fluorogenic substrate libraries"*, PNAS (2000), 97 (14) 7754-7759, may be used.

To avoid "cross talk" effects and to detect protease activity, the specificity of the substrates may be enhanced by use of steric restrictor library construction techniques and fluorescence label/quencher techniques discussed previously. This library of SR-peptides is then spotted onto a microarray using previously discussed techniques.

In use, several identical microarrays may be used in parallel to gain additional information. For example, assume the system is being used to analyze a tumor. A tissue biopsy that has been solubilized by suspension in a physiological buffer solution is used as the sample. In this example, three identical microarrays would be used. One microarray is exposed to a high concentration of the sample, a second microarry is exposed to a diluted concentration of the sample, and a third microarray is exposed to the sample with an added "protease cocktail" mixture containing low concentrations of active proteases against the various protease substrates on the array.

In this example, the reaction kinetics of all three microarrays would then be monitored. Ideally this monitoring would be done in parallel with a reader system capable of monitoring multiple mircoarrays simultaneously. This would enhance the ability of the microarray system to detect short-lived proteases and short-lived protease modifying agents. Example results of such an example assay of this type are shown on Table 2.

TABLE 2

Activity of an exemplary angiogenesis protease microarray. In this table, a "+" signifies higher activity than expected for a control tissue, and a "−" signifies lower activity than expected for a control tissue. Results where there are no significant deviations from a control tissue are left blank. Here, the "cocktail" column signifies a microarray where a dilute mixture containing proteases with specificity against all of the array elements has been added to the tissue sample, as a test for protease inhibiting factors. Here, only a portion of the angiogenesis protease regions are shown.

| | Highly metastatic tumor high positive angiogenesis, low levels of angiogenic inhibitors | | | Low metastatic tumor low positive angiogenesis, high levels of angiogenic inhibitors | | |
|---|---|---|---|---|---|---|
| Protease substrate | High | Low | Cocktail | High | Low | Cocktail |
| TGF-β activation | + | | | + | | |
| Matrix bFGF release | + | | | + | | |
| Matrix VEGF release | + | | | + | | |
| Membrane TNF-α release | + | | | + | | |
| MCP-3 | | | | | | |
| pro-MMP-2, Plasminogen (MMP2) | + | + | + | − | + | − |
| Plasminogen (MMP3) | | | | | | |
| Plasminogen (MMP7) | | | | | | |
| Plasminogen (MMP9) | + | − | + | − | + | − |
| Plasminogen (MMP12) | | | | | | |
| u-PAR (MMP12) | − | − | + | + | − | + |
| Plasminogen (tPA) | | | | | | |
| Plasminogen (uPA) | | | | | | |
| Collagen IV (MMP2) | | | | | | |
| Collagen IV (MMP-9) | + | − | + | − | − | + |
| Collagen IV | | | | | | |
| Collagen IV | | | | | | |
| Collagen XV | | | | | | |
| Collagen XVIII | | | | | | |
| Cathepsin L | | | | | | |
| Collagen XVIII | | | | | | |
| Cathepsins | | | | | | |
| Collagen XVIII Elastase | | | | | | |
| Collagen XVIII MMP | | | | | | |
| Thrombospondin | | | | | | |
| Hyaluronan | | | | | | |
| SPARC | | | | | | |
| Prolactin | | | | | | |
| Platelet factor 4 | | | | | | |
| MMP-2 | | | | | | |
| Antithrombin III | | | | | | |
| Calreticulin | | | | | | |
| HMWKinnogen domain 5 | | | | | | |
| Endothelial cell thrombin receptor | | | | | | |
| Fibrin | | | | | | |
| Fibrin | | | | | | |
| TIMP-1, TIMP-2 | + | − | + | − | − | + |
| Cathepsin B | | | | | | |
| EGF | | | | | | |
| Fibrinoectin | | | | | | |
| Osteopontin | | | | | | |

A few examples of how the data from Table 2 might be interpreted, and used to aid in clinical decision making, will be given.

u-PAR activity results: It has been shown (Koolwijk, et. al. *Blood* (2000), 97(10):3123-31) that the protease MMP-12 may control angiogenesis through proteolysis of the urokinase-plasminogen activator receptor (u-PAR). In contrast to some of the other matrix metalloproteases, MMP-12 is characterized as an antiangiogenic protease (e.g. higher activity is correlated to lower angiogenesis). Thus higher MMP-12 levels correlate with lower angiogenic potential.

Note the u-PAR substrate example results in Table 2. Here the high metastatic tumor example has low activity at high concentrations. This low activity does not appear to be do to an endogenous inhibitor because the diluted sample continues to show negative activity, and the application of extra MMP-12 through the protease cocktail shows the expected increase in proteolytic activity. By contrast, the low metastatic tumor has high u-PAR activity, and the diluted example and cocktail examples are consistent with the theory that the MMP-12 protease in this sample simply has high levels of activity, with no extra inhibitors or stimulators present.

Since many matrix metalloproteases correlate with increased angiogenic activity, the normal course of treatment, if the microarray data was not available, might be to treat the low metastatic tumor in this example with a chemotherapeutic protease inhibitor against a broad spectrum of matrix metalloproteases. However in this case, the microarray results suggest that this standard treatment might be inappropriate.

Since it is undesirable to inhibit this MMP-12 activity, the microarray results would warn the physician that chemotherapy of the low metastatic tumor with a matrix-metalloprotease inhibitor with activity against MMP-12, could lead to unwanted stimulation of angiogenesis. The physician could then use this information to select an alternate chemotherapy regime.

As a second example, note the high level of proteolysis directed against the MMP-9 cleavage site on collagen IV in both tumor types. MMP-9 is generally considered to be an angiogenesis promoting protease (for a review, see McCawley and Matrisian, *Current Biology* (2001)11: R25-R27). Although based on the previous results, treatment of the low metastatic tumor with a broad-spectrum matrix-metalloprotease chemotherapeutic inhibitor drug would not be advised, the situation with the high metastatic tumor is different. Here the only matrix metalloproteases expressed are those generally correlated with high angiogenesis. Thus for this tumor, there is no downside to using a broad-spectrum chemotherapy inhibitor against many different matrix metalloproteases.

As a third example, in the high metastatic tumor case, consider the high level of activity against the Cathepsin-B specific protease site on the TIMP-1 and TIMP-2 substrate targets. TIMP-1 and TIMP-2 are endogenous inhibitors of Matrix Metalloproteins, and are generally correlated with angiogenic suppressive activity. Cathepsin-B is known to promote antiogenesis by degrading these endogenous inhibitors. Here, the results suggest that use of a chemotherapeutic protease inhibitor that blocks Cathepsin-B activity (such as a drug similar to CA074, an in-vitro Cathepsin-b inhibitor) might be effective for the high metastatic tumor. By inhibiting Cathepsin B activity, TIMP degradation can be reduced, and the natural inhibitory effects of the TIMP-1, and TIMP-2 inhibitors can help keep angiogenesis in check.

By contrast, the low metastatic tumor in this example has both a low level of activity against the Cathepsin-B protease site on TIMP-1 and TIMP-2, and evidence of high levels of TIMP-1 and TIMP-2 inhibition (showing up in Table 2 as inhibiton of both the MMP-1 specific region on the pro-MMP-2 substrate target, and the MMP-9 specific region on the Plasminogen and Collagen IV substrate targets). The triple microarray system detects this inhibition by the higher levels of activity seen in diluted samples, and also by the inhibition of the MMP-1 and MMP-9 proteases supplied in the protease cocktail mix. The results suggest that anti-Cathepsin-B chemotherapy is not needed for the low metastatic tumor.

In this example, by combining data from all three findings, a physician would know that an effective treatment against the high metastatic tumor would combine a broad-spectrum matrix metalloprotease inhibitor with a Cathepsin-B inhibitor. By contrast, the physician would also know that broad-spectrum matrix metalloprotease inhibitors are contraindicated for the low metastatic tumor.

In addition to tumor vascularization, angiogenesis and complex protease systems are involved in many other physiological processes. Other assays where these techniques may be applied include assays for arthritis, vascular proliferative disorders, coagulation disorders, sepsis, microbial assays, and many other diseases.

High throughput Drug Screening Assays

Protease substrate microarrays have natural applications to the characterization and high-throughput screening of various candidate protease inhibitor or activity modifier drugs. Ideally, a promising drug candidate will be extremely selective at inhibiting or modifiying the activity of only the target protease, while having minimal or no impact on non-target proteases. In particular, such techniques can be used for discriminating between a large number of alternate drug candidates, and selecting those candidates that have the desired specificity.

In one type of drug candidate optimization study, a protease mixture containing a target protease and typically many non-target proteases is exposed to a candidate drug, and analyzed on a microarray containing many protease targets. The resulting spectrum of anti-protease activity is examined. In this example, assuming that the desired drug will high specificity against just the target protease, an optimized candidate inhibitor will specifically inhibit just the target protease, while not impacting the non-target proteases.

Figure 9:
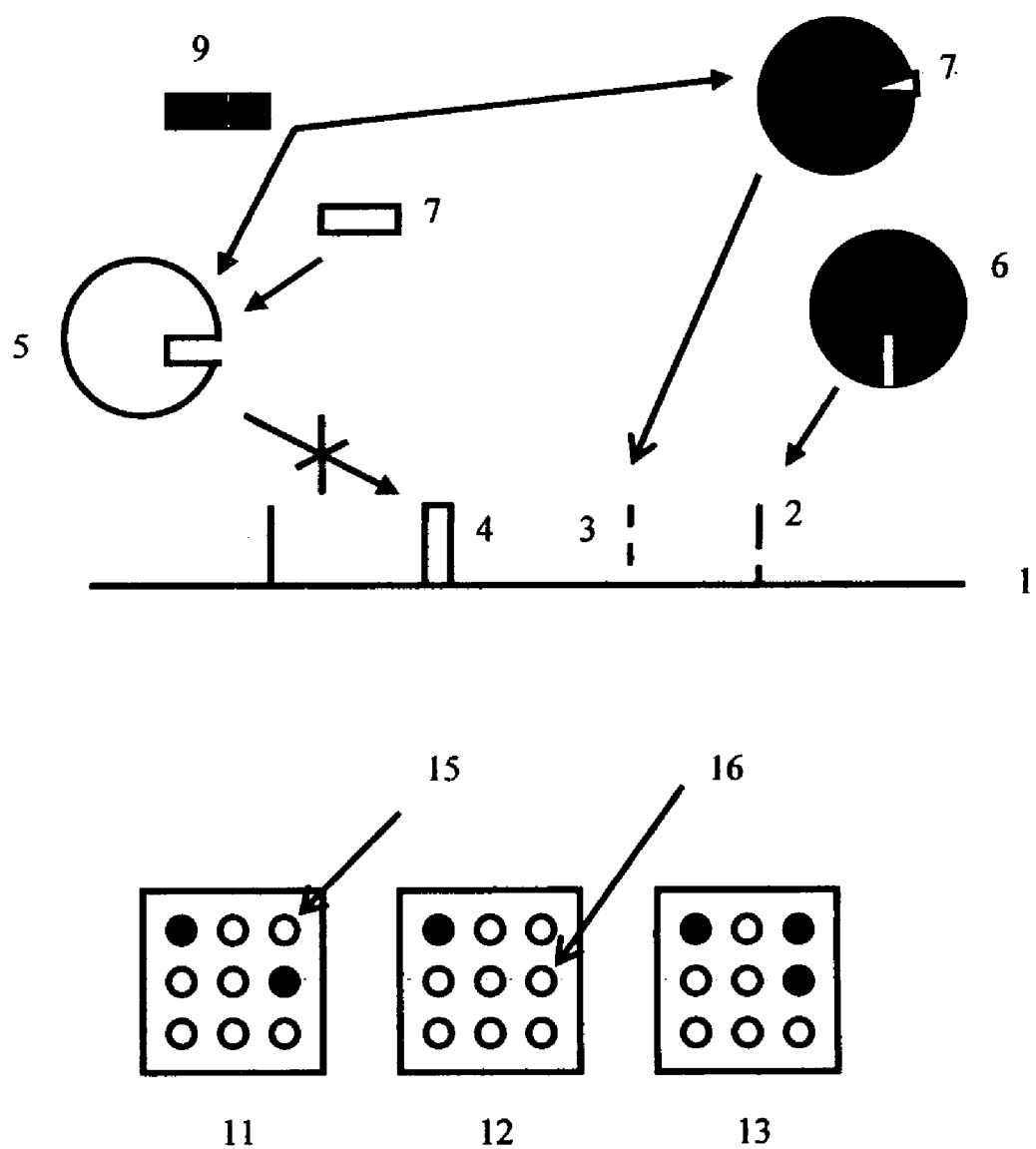
FIG. 9 shows an application for high-throughput protease inhibitor optimization and characterization

FIG. 9 shows an application in monitoring the differential effects of a candidate protease inhibitor on a variety of different proteases. Here protease substrate microarrays with a wide variety of potential protease substrates are exposed to a mixture of proteases.

This mixture will include the target protease, and also a variety of non-target proteases and other relevant biological molecules. The protease mixture may be synthetic in origin (e.g. a mixture of purified proteases), or natural in origin (e.g. tissue fluid, whole cell homogenates, etc.) from the natural biochemical environment where the candiate drug is expected to function.

In FIG. 9, the microarrays (1) are composed of various protese substrate peptides. Some peptides (4) monitor the protease acivity expected from the enzyme that the drug is targeted against. Other peptides (2,3) monitor the drugs effect on non-target proteases. The microarrays are exposed to a sample containing the drug target protease (5) and one or more non-target proteases (6, 7). Ideally, many microarrays are used, for example, one for each drug candidate (or set of drug candidates), and at least one control.

Here, the example shows a simplified drug screening assay using three identical microarrays (11, 12, 13), with one target protease (5) with activity against peptide (4), and two non-target proteases (6, 7) with activity against peptides (2, 3). In this assay a "good" drug candidate (8) that specifically inhibits the target enzyme (5); a "bad" drug candidate that inhibits both the target protease (5) and a non-target protease (7); and a control (no drug) are screened on microarrays (11, 12, and 13) respectively.

In this example, A "good" drug candidate, run on microarray (11), will show inhibiton of just the target protease activity (15). A "poor" drug candidate, run on microarray (12), will show inhibition of the target protease, and additional and undesired inhibition of one or more non-target proteases (16). The control microarray (13), running without the candidate protese inhibitor, shows activity from all three proteases.

In practice, it is expected that a large number of alternate candidate drugs will be tested on a large number of microarrays. With these methods, thousands of candidate drugs can be tested for specific activity against one specific enzymatic target out of hundreds or even thousands of non-target enzymes. This results in an efficient high-throughput drug screening system. Note that although these examples focus on proteases, protease targets, and drugs with activity against proteases, it should be appreciated that the enzyme substrate microarray methods taught herein can be applied to other types of enzymes as well.

Alternatively, the arrays may also be useful for drugs that affect the allosteric sites on proteases. Here, a protease can be incubated with or without a candidate allosteric modification drug, and the effect of the candidate drug on the protease's specificity can be rapidly determined. Here the assay is focused on detecting a change in protese activity, rather than detecting inhibition of protease activity. This is shown in FIG. 10.

Figure 10:
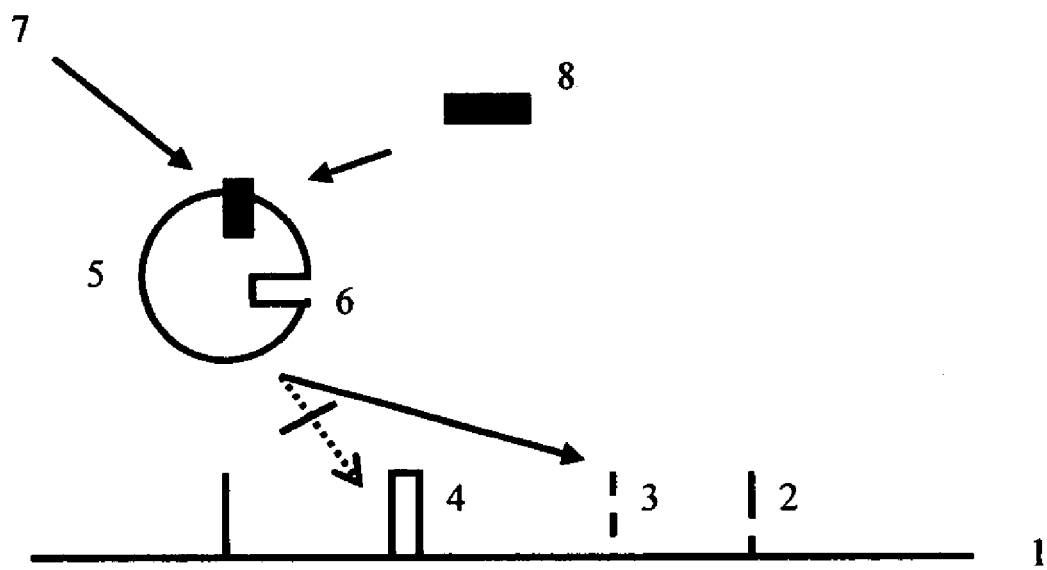
FIG. 10 shows an application for the microarray for discovery of protease activity modifying agents
Figure 10:
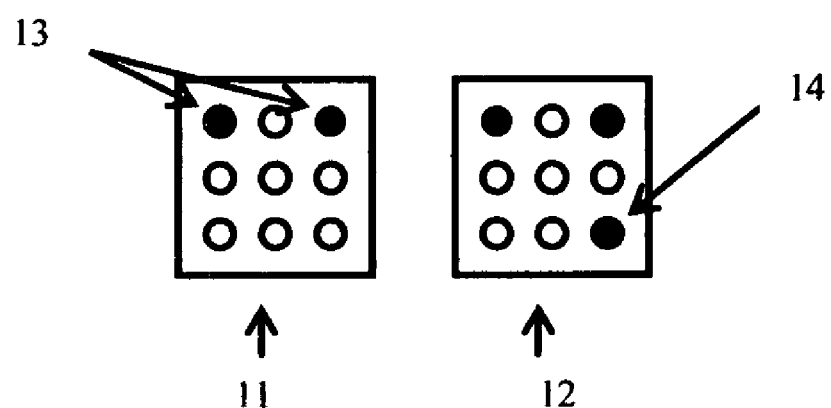

In FIG. 10, microarrays (1) containing peptide targets that are reactive to the protease without an allosteric modifying agent (4); targets reactive to the protease in the presence of an allosteric modiying agent (3); and peptides unreactive to the protese in either configuration (2) are used.

In this assay, protease (5) with active site (6) and allosteric site (7) is exposed to allosteric modifying agent (8) in test microarray (12); and not exposed to the allosteric modifying agent (8) in a control microarray (11).

The case where allosteric modifying agent (8) sucessfully induces protease (5) to change its specificity from peptide (4) to peptide (3) is shown in (11) and (12). The enzyme's activity in the absence of the allosteric agent is identified by the peptides localized in zones (13). The effects of the allosteric agent are shown in (12). Here, in addition to the original spectrum of protease specificity, a new specificity has been induced by the agent. This is identified by the peptides shown in (14).

Additional control experiments can be done (not shown), such as adding the allosteric agent in the absence of the target enzyme, to demonstrate that the allosteric agent itself is not the direct cause of the new proteolytic activity.

As an additional example of the use of such microarrays in drug discovery, consider the coagulation protease system. Coagulation proteases have multiple functions and specificities. One is to activate the clotting cascade; the other is to serve as a reservoir of angiogenesis modifying factors. These angiogenic factors reside on sections of the coagulation protease's peptide chain. When attached to the protease, these factors are inactive, but when cleaved from the coagulation protease by the action of an "anti-protease protease", the angiogenesis factors become active. In the inactive form, these are referred to as "cryptic" angiogenic factors.

The protease microarrays of this invention may also be useful in developing allosteric drugs that don't affect the pro-coagulation activity of the coagulation protease, but do affect the proteolytic susceptibility of the cryptic angiogenic site on the coagulation protease. Such drugs could be potentially useful as another safe way to control angiogenesis.

Alternatively, by interfering with the allosteric effects of the clotting cascade proteases, novel anticoagulant drugs may be developed to allow precise specificity and control over the clotting cascade. Allosteric agents have a profound effect on the regulation of coagulation, and undoubtedly many other biologically significant protease regulatory systems as well, and thus such methods may be extended to many other physiological processes.

As another example, thrombin has multiple and different allosteric sites for procoagulant activators, cell surface thrombin receptors, and protein c. This was demonstrated by Leung and Hall, *Trends Cardiovasc Med* 2000 February; 10(2): 89-92, who generated a series of thrombin mutants and demonstrated one mutant that had lost its procoagulant activities while retaining its ability to activate protein c. They found that different domains were involved in thrombin's interaction with thrombomodulin. By using methods disclosed here, candidate allosteric drugs may be screened. Here the array would have a variety of different target peptides, including target peptides selected from the "intrinsic pathway proteases, extrinsic pathway proteases, as well as sites from protein c, thrombomodulin, the sites cleaved to produce the angiogenesis factors, and other thrombin targets. Drug candidates that specifically affect only the desired target could be selected by the microarray methods of this invention.

Other examples taken from the coagulation system include the allosteric effects of tissue factor on factor VIIa, the allosteric mechanism by which the anticoagulant effects of heparin are mediated, and the allosteric effects of Hirugen on tissue type plasminogen activator.

As a final example, consider a protease substrate microarray used for apoptosis drug discovery. As previously discussed, apoptosis is mediated by a complex network of proteolytic enzymes, including over ten different caspases, over ten different caspase inhibitors, and over 10 different caspase promoters. In particular, caspases may be regulated by the "inhibitor of apoptosis protein" (IAP) family (for review, see Verhagen et. al., *"inhibitor of apoptosis proteins and their relatives: IAPs and other BIRPs. Genome Biology* (2001) 2(7) reviews 3009.1-3009-10). Inappropriate apoptosis is involved in many different disorders, including Alzheimer's disease, brain and spinal cord injury, myocardial infarction, cancer, and many other diseases. As a result, caspases and caspase activity modulators are of high current interest as a therapeutic target for new drug development. (McBride et. al., *Emerging therapeutic targets in Caspase-dependent disease, Emerging Therapeutic Targets* (1999), 3(3) 391-411).

Here, an apoptosis protease microarray would consist of the various proteolytic sites involved in caspase activation, (e.g. on the caspase proenzyme structures), as well as the various caspase target proteolytic sites (e.g. nuclear lamins, cytoskeletal proteins, PAK2 kinases, etc.). A number of these targets were reviewed in Hengartner (2000), *Nature* 407, 770-776. As before, these protease substrate target regions would be synthesized, have their specificity enhanced by steric restrictor groups, and bound to microarrays.

Consider the case where a drug is desired that promotes apoptosis in certain cell populations. Here, such a drug might work by "inhibiting the caspase inhibitors". To screen for such a drug, an apoptosis protease microarray might be used in conjunction with cytoplasmic extracts from the desired cell targets, as well as a cocktail of purified caspases. In such a situation, a candidate drug might be found by using a panel of six identical microarrays, each microarray being challenged with different combination mixtures of the candidate drug, a cell extract from non-apoptic state cell populations, and a purified caspase protease cocktail.

In this experiment, a promising candidate drug might show a pattern similar to Table 3 below:

TABLE 3

Apoptosis drug discovery using a panel of six identical apoptosis protease microarrays exposed to different conditions. (Here, only portions of the microarray's protease substrate regions are shown.)

| Protease region on microarray | Protease cocktail alone | Cell extract alone | Protease cocktail and cell extract | Drug with protease cocktail alone | Drug with cell extract alone | Drug with cell extract and protease cocktail |
|---|---|---|---|---|---|---|
| pro-caspase-9 | + | − | − | + | − | − |
| pro-caspase-8 | + | − | − | + | − | + |
| pro-caspase-3 | + | − | + | + | − | + |
| pro-caspase-7 | + | − | + | + | − | + |
| caspase-9 substrate | + | − | − | + | − | + |
| caspase-8 substrate | + | − | + | + | − | + |
| caspase-3 substrate | + | − | + | + | − | + |
| caspase-7 substrate | + | − | + | + | − | + |

Here, the protease cocktail by itself has full ability to cleave all caspase targets. Further, the non-apoptic cell extract has no detectable caspase activity. However when combined with the protease cocktail, the reasons for the non-apoptic state of the cell population become clear. The cell extract from this population contains inhibitors that prevent the activation of both pro-caspase-9 and pro-caspase-8, the two-initiator proteases of apoptosis.

Further, it may be seen that although the candidate drug has no effect on the activity of the caspases itself, it is able to overcome the inhibitory effect of the cell extract on the conversion of pro-caspase-8 to active caspase-8. Such a drug would be a promising candidate for further study.

The invention claimed is:

1. A synthetic enzyme substrate, comprising:
   a peptide substrate moiety capable of independently serving as a substrate for a target protease that cleaves a bond between two amino acids of said peptide substrate moiety;
   a first and second streric restrictor group, wherein the N-terminus and C-terminus of said peptide substrate moiety are each covalently coupled to one of said steric restrictor groups, wherein said steric restrictor groups are polymers comprised of two or more non-identical D-amino acid monomers, wherein the sequences of said D-amino acid monomers of each of said steric restrictor groups are selected based upon the ability of said restrictor groups to protect said peptide substrate from serving as a substrate for non-target proteases, while preserving the ability of said peptide substrate to serve as a substrate for said target protease;
   wherein a first label moiety incorporated into said first steric restrictor group produces a detectable signal that is quenched by a second label moiety incorporated into said second steric restrictor group, and in which enzymatic cleavage of the peptide substrate moiety by said target protease produces a change in the detectable signal.

2. The synthetic substrate of claim 1, in which the first label moiety is a fluorophore, and the second label moiety note to quench the fluorescence of the first label moiety.

3. The synthetic substrate of claim 1, wherein said substrate is bound to a solid support, and used as an assay device for protease activity.

* * * * *